(12) United States Patent
Mach

(10) Patent No.: US 12,236,800 B2
(45) Date of Patent: Feb. 25, 2025

(54) LOCKING MEMBER FOR AN INJECTION DEVICE AND AN INJECTION DEVICE TRAINER

(71) Applicant: Janssen Pharmaceuticals, Inc., Titusville, NJ (US)

(72) Inventor: Hung Mach, Flushing, NY (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 895 days.

(21) Appl. No.: 16/585,465

(22) Filed: Sep. 27, 2019

(65) Prior Publication Data

US 2020/0101227 A1  Apr. 2, 2020

(30) Foreign Application Priority Data

Oct. 1, 2018  (GB) ...................................... 1816035

(51) Int. Cl.
*G09B 23/28* (2006.01)
*A61M 5/20* (2006.01)
*A61M 5/32* (2006.01)

(52) U.S. Cl.
CPC ......... *G09B 23/285* (2013.01); *A61M 5/2033* (2013.01); *A61M 5/3204* (2013.01);
(Continued)

(58) Field of Classification Search
CPC .......... G09B 23/285; A61M 2005/208; A61M 2005/2086; A61M 5/3243;
(Continued)

(56) References Cited

U.S. PATENT DOCUMENTS

| | | | |
|---|---|---|---|
| 3,656,480 A  * | 4/1972 | Rubricius | ......... A61M 5/31513 |
| | | | 604/218 |
| 5,300,030 A | 4/1994 | Crossman et al. | |

(Continued)

FOREIGN PATENT DOCUMENTS

| | | |
|---|---|---|
| CH | 709126 | 7/2015 |
| CN | 104661696 A | 5/2015 |

(Continued)

OTHER PUBLICATIONS

International Search Report for PCT/IB2019/058249 dated Jan. 10, 2020.

(Continued)

*Primary Examiner* — James D Ponton
(74) *Attorney, Agent, or Firm* — Craig M. Brown

(57) ABSTRACT

An injection device and an injection device trainer for training a user to use an injection device. Each one of the injection device and the injection device trainer can include: a body portion; an actuator positioned towards a proximal end of the body portion, the actuator moveable from a proximal position to a distal position; a shield positioned towards a distal end of the body portion, the shield moveable between: an initial position; a retracted position that is more proximal relative to the body portion than the initial position; and an extended position that is more distal relative to the body portion than the initial position; and a locking member rotatable between a first orientation in which the locking member resists movement of the actuator from the proximal position to the distal position; and a second orientation in which the locking member permits the actuator to move from the proximal position to the distal position.

40 Claims, 17 Drawing Sheets

(52) U.S. Cl.
CPC . *A61M 2005/206* (2013.01); *A61M 2005/208* (2013.01); *A61M 2005/3217* (2013.01); *A61M 2205/58* (2013.01)

(58) Field of Classification Search
CPC ............ A61M 5/31501; A61M 5/2033; A61M 5/3204; A61M 2005/206; A61M 2005/3217; A61M 2205/58; A61M 5/326; A61M 2005/2013; A61M 2005/3267; A61M 5/20; A61M 5/31566; A61M 5/3157; A61M 5/31571; A61M 5/31578; A61M 5/3202; A61M 5/321; A61M 5/3245; A61M 5/502; A61M 2005/3143; A61M 2005/3247; A61M 2005/3254; A61M 2005/5033
See application file for complete search history.

(56) References Cited

U.S. PATENT DOCUMENTS

| | | | |
|---|---|---|---|
| 8,491,530 | B2 | 7/2013 | Maritan |
| 8,932,266 | B2 | 1/2015 | Wozencroft |
| 9,022,982 | B2 | 5/2015 | Karlsson et al. |
| 9,443,445 | B2* | 9/2016 | Laurusonis .......... G09B 23/285 |
| 10,279,130 | B2 | 5/2019 | Mosebach et al. |
| 11,260,176 | B2 | 3/2022 | Hansen |
| 11,484,667 | B2 | 11/2022 | Stefanov |
| 2005/0101919 | A1 | 5/2005 | Brunnberg |
| 2007/0191785 | A1 | 8/2007 | Barere et al. |
| 2011/0054414 | A1 | 3/2011 | Shang et al. |
| 2011/0077589 | A1 | 3/2011 | Karlsson et al. |
| 2011/0092915 | A1 | 4/2011 | Olson et al. |
| 2012/0015336 | A1* | 1/2012 | Mach .................. G09B 23/285 434/262 |
| 2013/0281939 | A1 | 10/2013 | Roberts et al. |
| 2013/0317428 | A1 | 11/2013 | Brereton et al. |
| 2014/0155826 | A1 | 6/2014 | Yevmenenko et al. |
| 2015/0273161 | A1 | 10/2015 | Bengtsson et al. |
| 2016/0317749 | A1 | 11/2016 | Jugl et al. |
| 2016/0335920 | A1* | 11/2016 | Bendek ................ G09B 23/285 |
| 2017/0069230 | A1 | 3/2017 | Baker et al. |
| 2017/0148354 | A1 | 5/2017 | Baker et al. |
| 2017/0165429 | A1 | 6/2017 | Holmqvist et al. |
| 2017/0227844 | A1 | 11/2017 | Baker et al. |
| 2017/0337844 | A1* | 11/2017 | Baker ................... G09B 19/24 |
| 2017/0337845 | A1 | 11/2017 | Su |
| 2018/0008776 | A1 | 1/2018 | Ogawa et al. |
| 2018/0161518 | A1 | 6/2018 | Shluzas et al. |
| 2018/0211562 | A1 | 7/2018 | Rios et al. |
| 2018/0233066 | A1 | 8/2018 | Lettman et al. |
| 2019/0298934 | A1 | 10/2019 | Saussaye et al. |
| 2020/0101233 | A1 | 4/2020 | Mach |
| 2021/0268198 | A1 | 9/2021 | Baker et al. |
| 2023/0112983 | A1 | 4/2023 | Bendek et al. |

FOREIGN PATENT DOCUMENTS

| | | |
|---|---|---|
| CN | 105164741 A | 12/2015 |
| CN | 108352131 A | 7/2018 |
| EP | 2488237 A2 | 8/2012 |
| EP | 2968768 | 1/2016 |
| FR | 3056916 | 4/2018 |
| JP | 2015031784 A | 2/2015 |
| RU | 2438721 C2 | 1/2012 |
| TW | 201733629 A1 | 1/2017 |
| WO | WO 2014/033195 | 3/2014 |
| WO | WO 2014/150201 | 9/2014 |
| WO | WO 2014/164948 | 10/2014 |
| WO | WO 2015/028394 | 3/2015 |
| WO | WO 2016/176785 | 11/2016 |
| WO | WO 2018/111814 | 6/2018 |
| WO | WO 2018/172223 A1 | 9/2018 |

OTHER PUBLICATIONS

International Search Report for PCT/IB2019/058250 dated Dec. 3, 2019.

International Search Report for PCT/IB2019/058251 dated Dec. 18, 2019.

* cited by examiner

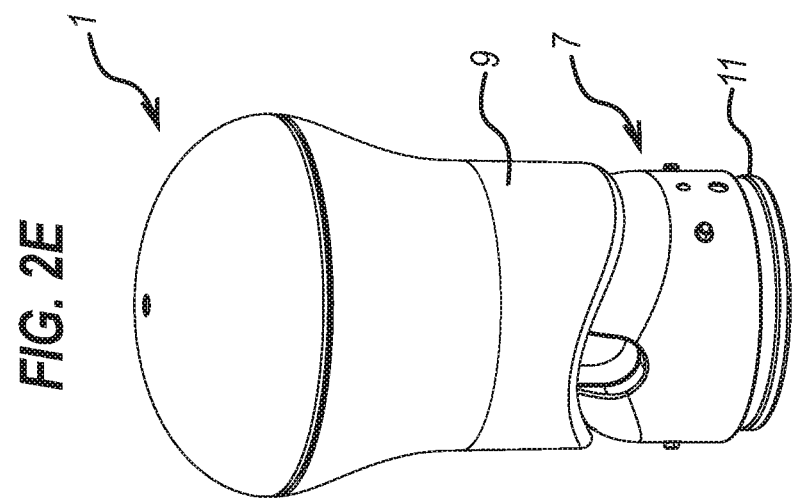
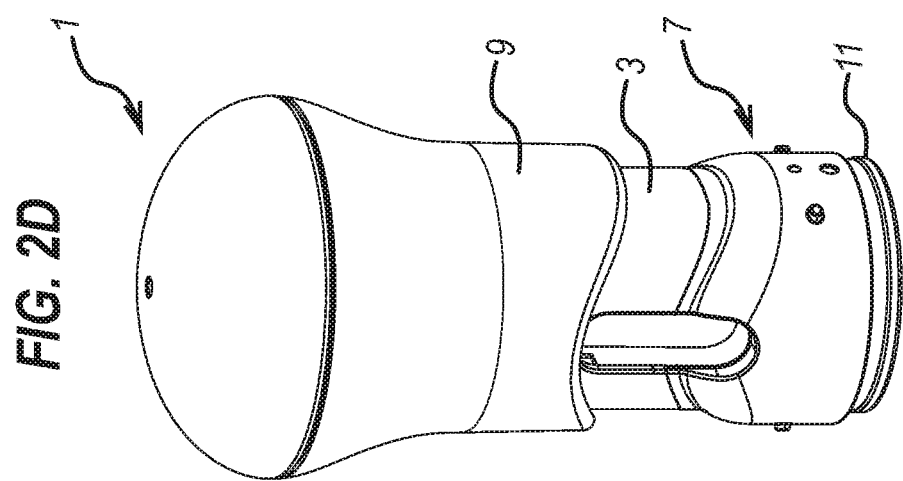
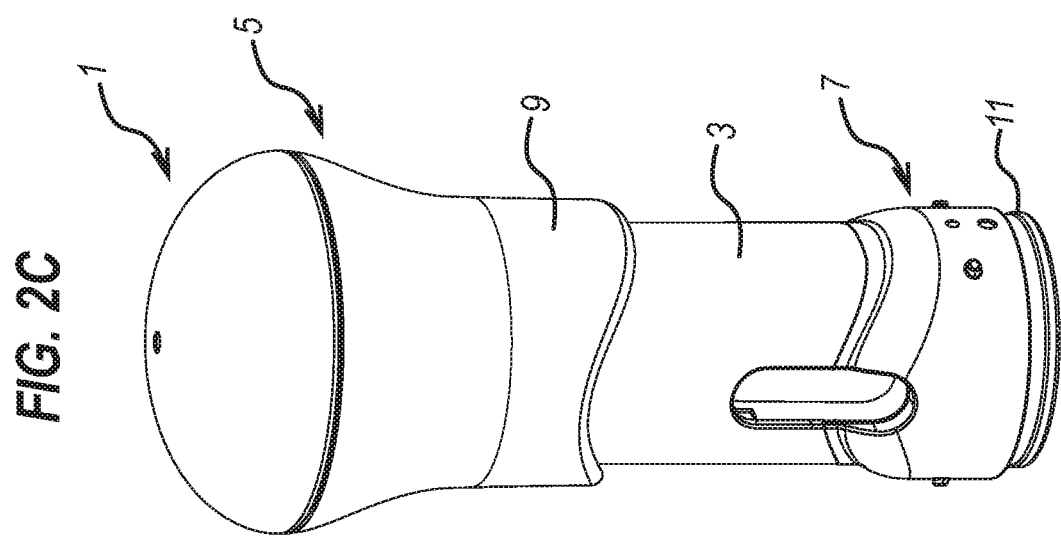

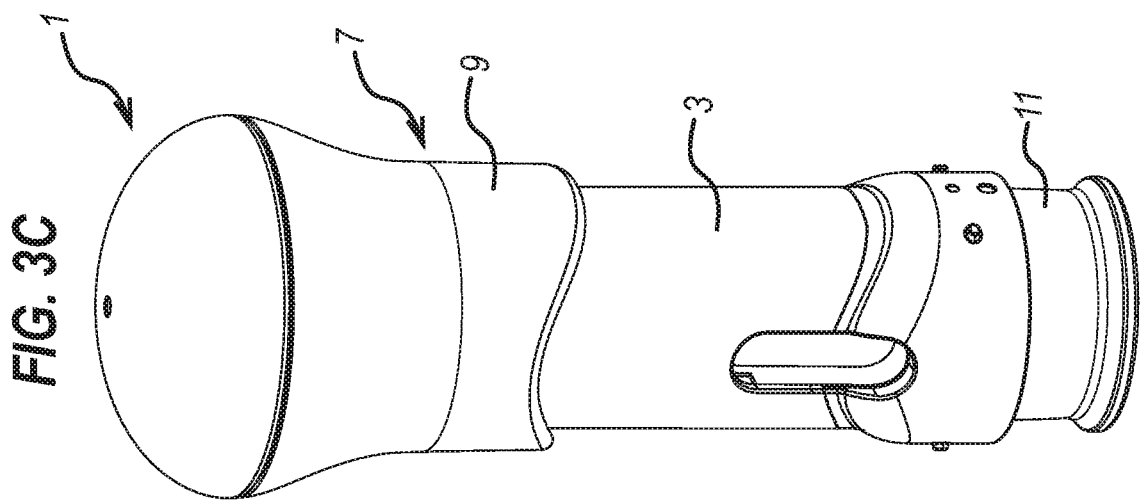
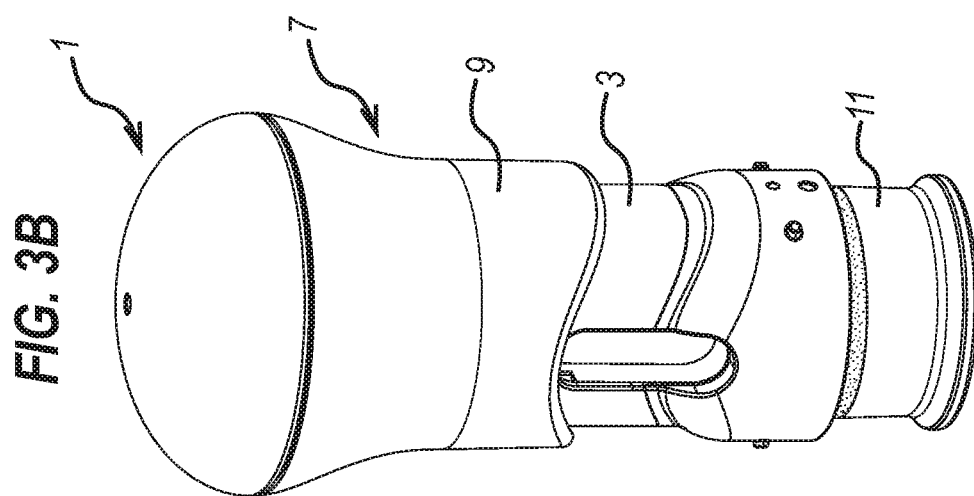
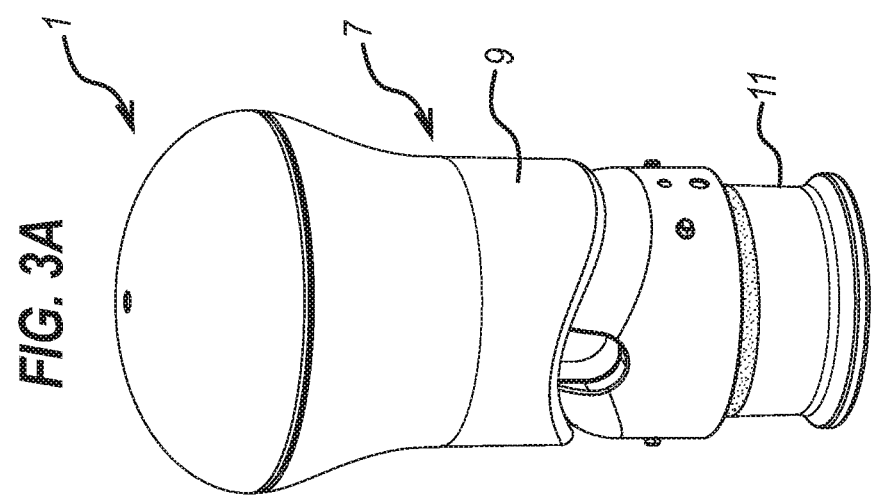

LOCKING MEMBER FOR AN INJECTION DEVICE AND AN INJECTION DEVICE TRAINER

TECHNICAL FIELD

This disclosure relates to an injection device for administering an injection and an injection device trainer for training a user to use an injection device.

BACKGROUND

It is desirable to be able to administer injections simply and safely when treating a patient. A conventional syringe for administering injections includes a barrel for holding medicament, a plunger that fits within the barrel and a needle through which the medicament is expelled when the plunger is pushed inside the barrel. Typically, the syringe will have a cap for shielding the needle when the syringe is not being used to administer an injection, which can be removed in order to expose the needle.

A specific problem with a conventional syringe is that a patient might accidentally stick themselves, or someone else, with the needle before administering the injection. Another specific problem is that it can be difficult to align the needle with the target site correctly, and thus an injection might be administered in the wrong place. Therefore, conventional syringes can be complicated and potentially unsafe to use, particularly for patients with limited dexterity.

Injection devices exist that have been designed to overcome these issues with conventional syringes. One such device includes a needle shield and a plunger which can be actuated in order to force medicament from the needle and into the patient. The needle shield retracts when pressed against the target site in order to expose the needle, and the plunger can be pressed at the same time for administering the injection. This allows the injection to be administered in a single motion by pressing the plunger of the device down onto the target site. This allows a patient to administer themselves with an injection in a safe and simple manner. Often these devices are designed so that they can be used only once, for instance by locking the needle shield in a position that covers the needle once the injection is complete. This prevents a patient from using a needle more than once, which has hygiene and health benefits.

An issue with known injections devices is that it can be difficult to train a patient on the use of these devices without actually administering an injection. Therefore, proper training may be limited to times when an injection is required. Alternatively, a non-active ingredient could be used as the substance for injection during training. However, unnecessarily injecting people should be avoided for health and hygiene reasons.

In light of the above, there is a need for a device that can be used to train a patient to use an injection device in a simple and safe manner. In addition, it is desirable for such a device to be used multiple times, so that multiple instances of training can be conducted using the same device. There is also a need for an injection device that has a simple construction and operates in a reliable manner.

SUMMARY

In one aspect of the invention, there is an injection device trainer for training a user to use an injection device, the injection device trainer comprising a body portion, an actuator positioned towards a proximal end of the body portion, the actuator moveable from a proximal position to a distal position, a shield positioned towards a distal end of the body portion, the shield moveable between: an initial position; a retracted position that is more proximal relative to the body portion than the initial position; and an extended position that is more distal relative to the body portion than the initial position, and a locking member rotatable between a first orientation in which the locking member resists movement of the actuator from the proximal position to the distal position; and a second orientation in which the locking member permits the actuator to move from the proximal position to the distal position. The first orientation of the locking member is configured to hold the shield in the initial position such that the shield is prevented from moving from the initial position to the extended position, and permits movement of the shield from the initial position to the retracted position. The shield is configured to contact with the locking member when moving from the initial position to the retracted position in order to move the locking member from the first orientation to the second orientation. Movement of the actuator by a first distance towards the distal position unlocks the shield from the locking member such that the shield is allowed to move towards the extended position.

Therefore, the injection device trainer accurately simulates use of an injection device which improves the training process. In addition, the user can practice administering an injection more times than in comparison to the situation in which training is only possible when a real injection is required. The locking member provides a mechanism for simulating use of the injection device.

In another aspect of the invention, there is an injection device comprising, a needle coupled with a chamber for storing fluid, a body portion, an actuator positioned towards a proximal end of the body portion, the actuator moveable from a proximal position to a distal position for dispensing fluid stored in the chamber from the needle, a shield positioned towards a distal end of the body portion, the shield moveable between: an initial position in which the shield covers the needle; a retracted position in which the shield exposes the needle, wherein the retracted position is more proximal relative to the body portion than the initial position; and an extended position in which the shield covers the needle, wherein the extended position is more distal relative to the body portion than the initial position, and a locking member rotatable between a first orientation in which the locking member resists movement of the actuator from the proximal position to the distal position; and a second orientation in which the locking member permits the actuator to move from the proximal position to the distal position. The first orientation of the locking member is configured to hold the shield in the initial position such that the shield is prevented from moving from the initial position to the extended position, and permits movement of the shield from the initial position to the retracted position. The shield is configured to contact the locking member when moving from the initial position to the retracted position in order to move the locking member from the first orientation to the second orientation. Movement of the actuator by a first distance towards the distal position unlocks the shield from the locking member such that the shield is allowed to move towards the extended position.

This provides a construction for the injection device that assists with reliability and ease of manufacture.

In another aspect of the invention, there is a method for training a user to use an injection device, the method comprising providing an injection device trainer comprising, a body portion, an actuator positioned towards a proximal end of the body portion, the actuator moveable from a proximal position to a distal position, a shield positioned towards a distal end of the body portion, the shield moveable between: an initial position; a retracted position that is more proximal relative to the body portion than the initial position; and an extended position that is more distal relative to the body portion than the initial position, and a locking member rotatable between a first orientation in which the locking member resists movement of the actuator from the proximal position to the distal position; and a second orientation in which the locking member permits the actuator to move from the proximal position to the distal position. The first orientation of the locking member is configured to hold the shield in the initial position such that the shield is prevented from moving from the initial position to the extended position, and permits movement of the shield from the initial position to the retracted position. The method further comprises moving the shield from the initial position to the retracted position so that the shield contacts with the locking member in order to move the locking member from the first orientation to the second orientation, and moving the actuator by a first distance towards the distal position to unlock the shield from the locking member such that the shield moves towards the extended position.

In another aspect of the invention, there is a method of administering an injection, the method comprising providing an injection device comprising, a needle coupled with a chamber for storing fluid, a body portion, an actuator positioned towards a proximal end of the body portion, the actuator moveable from a proximal position to a distal position for dispensing fluid stored in the chamber from the needle, a shield positioned towards a distal end of the body portion, the shield moveable between: an initial position in which the shield covers the needle; a retracted position in which the shield exposes the needle, wherein the retracted position is more proximal relative to the body portion than the initial position; and an extended position in which the shield covers the needle, wherein the extended position is more distal relative to the body portion than the initial position, and a locking member rotatable between a first orientation in which the locking member resists movement of the actuator from the proximal position to the distal position; and a second orientation in which the locking member permits the actuator to move from the proximal position to the distal position. The first orientation of the locking member is configured to hold the shield in the initial position such that the shield is prevented from moving from the initial position to the extended position, and permits movement of the shield from the initial position to the retracted position. The method further comprises moving the shield from the initial position to the retracted position so that the shield contacts the locking member in order to move the locking member from the first orientation to the second orientation, and moving the actuator by a first distance towards the distal position to unlock the shield from the locking member such that the shield moves towards the extended position.

In another aspect of the invention, there is provided an injection device trainer for training a user to use an injection device, the injection device trainer comprising, a body portion and an actuator positioned towards a proximal end of the body portion, the actuator moveable from a proximal position to a distal position. The body portion comprises a body protrusion and the actuator comprises a latch that is arranged to couple with the body protrusion when the actuator is in the distal position, thus holding the actuator in the distal position.

In this way, coupling of the latch to the body protrusion indicates that the actuator has reached the distal position which simulates completion of an injection being administering by an injection device. Therefore, the user can be trained to determine that an injection has been administered properly.

In another aspect of the invention, there is provided an injection device comprising a needle coupled with a chamber for storing fluid, a body portion, and an actuator positioned towards a proximal end of the body portion, the actuator moveable from a proximal position to a distal position for dispensing fluid stored in the chamber from the needle. The body portion comprises a body protrusion and the actuator comprises a latch that is arranged to couple with the body protrusion when the actuator is in the distal position, thus holding the actuator in the distal position.

In this way, coupling of the latch to the body protrusion indicates that the actuator has reached the distal position which indicates completion of an injection being administering by the injection device. Therefore, the user can more accurately determine that the injection has been administered properly.

In another aspect of the invention, there is provided an injection device trainer for training a user to use an injection device, the injection device trainer comprising a body portion and an actuator positioned towards a proximal end of the body portion, the actuator moveable from a proximal position to a distal position. The body portion comprises a body protrusion and the actuator comprises a latch that is arranged to contact the body protrusion when the actuator is in the distal position and to emit an audible sound.

In this way, the audible sound indicates that the actuator has reached the distal position which simulates completion of an injection being administering by an injection device. Therefore, the user can be trained to determine that an injection has been administered properly. The audible sound may have an intensity that enables a user to hear the sound at 1 m away from the device, or at least at an arm's length from the device. The latch may be configured to emit an audible sound above a predetermined threshold intensity at a certain distance from the device (e.g. 30 cm). For example, the predetermined threshold intensity may be 40 dB, such that the intensity of the sound emitted is above the normal sound intensity of a quiet room. This enables the user to hear the sound in a normal working environment. The predetermined threshold intensity may be 50 dB, 60 dB or even 70 dB in order to ensure that the user can hear the sound in a variety of different environments. The sound may be in the form of a 'click', which is a short sound (e.g. less than a second long). The sound is emitted due to the mechanical interaction between the latch and the body protrusion, and is not emitted by an electronic device.

In another aspect of the invention, there is provided an injection device comprising a needle coupled with a chamber for storing fluid, a body portion, and an actuator positioned towards a proximal end of the body portion, the actuator moveable from a proximal position to a distal position for dispensing the fluid stored in the chamber from the needle. The body portion comprises a body protrusion and the actuator comprises a latch that is arranged to contact the body protrusion when the actuator is in the distal position and to emit an audible sound.

In this way, the audible sound indicates that the actuator has reached the distal position which indicates completion of an injection being administering by the injection device. Therefore, the user can more accurately determine that the injection has been administered properly.

In another aspect of the invention, there is a method for training a user to use an injection device, the method comprising providing an injection device trainer comprising a body portion and an actuator positioned towards a proximal end of the body portion, the actuator moveable from a proximal position to a distal position. The body portion comprises a body protrusion and the actuator comprises a latch. The method further comprises moving the actuator from the proximal position to the distal position so that the latch couples with the body protrusion when the actuator is in the distal position, thus holding the actuator in the distal position.

In another aspect of the invention, there is a method of administering an injection, the method comprising providing an injection device comprising a needle coupled with a chamber for storing fluid, a body portion, and an actuator positioned towards a proximal end of the body portion, the actuator moveable from a proximal position to a distal position for dispensing fluid stored in the chamber from the needle. The body portion comprises a body protrusion and the actuator comprises a latch. The method further comprises moving the actuator from the proximal position to the distal position so that the latch couples with the body protrusion when the actuator is in the distal position, thus holding the actuator in the distal position.

In another aspect of the invention, there is a method for training a user to use an injection device, the method comprising providing an injection device trainer comprising a body portion and an actuator positioned towards a proximal end of the body portion, the actuator moveable from a proximal position to a distal position. The body portion comprises a body protrusion and the actuator comprises a latch. The method further comprises moving the actuator from the proximal position to the distal position so that the latch contacts the body protrusion when the actuator is in the distal position and emits an audible sound.

In another aspect of the invention, there is a method of administering an injection, the method comprising providing an injection device comprising a needle coupled with a chamber for storing fluid, a body portion, and an actuator positioned towards a proximal end of the body portion, the actuator moveable from a proximal position to a distal position for dispensing the fluid stored in the chamber from the needle. The body portion comprises a body protrusion and the actuator comprises a latch. The method further comprises moving the actuator from the proximal position to the distal position so that the latch contacts the body protrusion when the actuator is in the distal position and emits an audible sound.

In another aspect of the invention, there is an injection device trainer for training a user to use an injection device, the injection device trainer comprising a body portion, an actuator positioned towards a proximal end of the body portion, the actuator moveable from a proximal position to a distal position, a shield positioned towards a distal end of the body portion, the shield moveable between: an initial position; an extended position that is more distal relative to the body portion than the initial position, and a connector that connects the actuator to the shield such that movement of the actuator from the distal position towards the proximal position pulls the shield from the extended position to the initial position.

In this way, it is possible to reset the injection device trainer back to the initial position such that the trainer can be used again. The connector provides a mechanism for achieving this function.

In another aspect of the invention, there is an injection device comprising a needle coupled with a chamber for storing fluid, a body portion, an actuator positioned towards a proximal end of the body portion, the actuator moveable from a proximal position to a distal position for dispensing fluid stored in the chamber from the needle, a shield positioned towards a distal end of the body portion, the shield moveable between: an initial position in which the shield covers the needle; a retracted position in which the shield exposes the needle, wherein the retracted position is more proximal relative to the body portion than the initial position; and an extended position in which the shield covers the needle wherein the extended position is more distal relative to the body portion than the initial position, and a connector that connects the actuator to the shield such that movement of the actuator from the distal position towards the proximal position pulls the shield from the extended position to the initial position.

In this way, it is possible to reset the injection device back to the initial position such that the injection device can be used more than once. The connector provides a mechanism for achieving this function.

In another aspect of the invention, there is a method for training a user to use an injection device, the method comprising providing an injection device trainer comprising, a body portion, an actuator positioned towards a proximal end of the body portion, the actuator moveable from a proximal position to a distal position, a shield positioned towards a distal end of the body portion, the shield moveable between: an initial position; an extended position that is more distal relative to the body portion than the initial position, and a connector that connects the actuator to the shield. The method further comprises moving the actuator from the distal position towards the proximal position in order to pull the shield from the extended position to the initial position using the connector.

In another aspect of the invention, there is a method of administering an injection, the method comprising providing an injection device comprising a needle coupled with a chamber for storing fluid, a body portion, an actuator positioned towards a proximal end of the body portion, the actuator moveable from a proximal position to a distal position for dispensing fluid stored in the chamber from the needle, a shield positioned towards a distal end of the body portion, the shield moveable between: an initial position in which the shield covers the needle; a retracted position in which the shield exposes the needle, wherein the retracted position is more proximal relative to the body portion than the initial position; and an extended position in which the shield covers the needle wherein the extended position is more distal relative to the body portion than the initial position, and a connector that connects the actuator to the shield. The method further comprises moving the actuator from the distal position towards the proximal position in order to pull the shield from the extended position to the initial position using the connector.

In another aspect of the invention, there is an injection device trainer for training a user to use an injection device, the injection device trainer comprising a body portion an actuator assembly positioned towards a proximal end of the body portion, the actuator moveable from a proximal position to a distal position, wherein the actuator assembly is coupled with a rotor, such that movement of actuator from the proximal position to the distal position causes the rotor to rotate, and a damping element coupled, or coupleable, to the rotor in order to damp the rotation of the rotor.

In this way, it is possible for the injection device trainer to simulate the resistance provided by the medicament in the injection device when the actuator is depressed.

In another aspect of the invention, there is an injection device comprising a needle coupled with a chamber for storing fluid a body portion, an actuator assembly positioned towards a proximal end of the body portion, the actuator moveable from a proximal position to a distal position for dispensing the fluid stored in the chamber from the needle, wherein the actuator assembly is coupled with a rotor, such that movement of the actuator from proximal position to the distal position causes the rotor to rotate, and a damping element coupled, or coupleable, to the rotor in order to damp the rotation of the rotor.

In this way, it is possible for the injection device to damp the progress of the actuator towards the distal position which ensures that the fluid is not dispensed from the needle too quickly.

In another aspect of the invention, there is a method for training a user to use an injection device, the method comprising providing an injection device trainer comprising a body portion, an actuator assembly positioned towards a proximal end of the body portion, the actuator moveable from a proximal position to a distal position, wherein the actuator assembly is coupled with a rotor, such that movement of actuator from the proximal position to the distal position causes the rotor to rotate, and a damping element coupled, or coupleable, to the rotor in order to damp the rotation of the rotor. The method further comprises moving the actuator from the proximal position to the distal position during which the damping element damps rotation of the rotor and thus damps movement of the actuator towards the distal position.

In another aspect of the invention, there is a method of administering an injection, the method comprising providing an injection device comprising a needle coupled with a chamber for storing fluid, a body portion, an actuator assembly positioned towards a proximal end of the body portion, the actuator moveable from a proximal position to a distal position for dispensing the fluid stored in the chamber from the needle, wherein the actuator assembly is coupled with a rotor, such that movement of the actuator from proximal position to the distal position causes the rotor to rotate, and a damping element coupled, or coupleable, to the rotor in order to damp the rotation of the rotor. The method further comprises moving the actuator from the proximal position to the distal position during which the damping element damps rotation of the rotor and thus damps movement of the actuator towards the distal position.

The locking member may comprise an actuator resistance surface that is arranged to resist movement of the actuator from the proximal position to the distal position, when the locking member is in the first orientation. The actuator resistance surface may comprise a protrusion extending from the locking member. The actuator may comprise an abutment surface that is arranged to abut the actuator resistance surface when the actuator is in the proximal position and the locking member is in the first orientation. The abutment surface may comprise a protrusion extending from the actuator. The locking member may comprise at least two (or a pair of) actuator resistance surfaces. The pair of actuator resistance surfaces may be located on opposite sides of the locking member with respect to one another. The actuator may comprise at least two (or a pair of) abutment surfaces. The pair of abutment surfaces may be located on opposite sides of the actuator with respect to one another. This simple and reliable mechanism enables the force exerted by the actuator on the locking member to be spread across the diameter of the locking member.

The locking member may comprise a cylindrical housing, and the actuator resistance surface may comprise a protrusion that protrudes from the surface of the cylindrical housing. The protrusion may span only partially around the circumference of the cylindrical housing. The locking member may comprise a ramp. The shield may comprise a ramp interface. The ramp interface of the shield may be arranged to interact with the ramp of the locking member when moving from the initial position to the retracted position in order to rotate the locking member from the first orientation to the second orientation. This provides a simple and reliable mechanism for rotating the locking member into the second orientation.

The locking member may comprise a third orientation in which the shield is allowed to move from the initial position to the extended position. The actuator may be configured to move by a first distance in order to move the locking member into the third orientation. In this way, the shield is prevented from moving to the extended position until the actuator has been at least partially depressed. The extended position simulates a locked-out state of an injection device, indicating that injection has been completed. Therefore, the trainer cannot simulate completion of the injection procedure until the actuator has been activated by the user.

The locking member may comprise a stop that is arranged to sit within a recess in the shield, thus holding the shield in the initial position. This provides a simple and reliable mechanism for keeping the shield in the initial position.

The stop may be arranged to move along a slot in the shield in order to allow the shield to move to the extended position. The stop may sit outside of the slot in the recess thus holding the shield in the initial position when the locking member is in the first orientation. In this way, the stop can be used to allow the shield to move from the initial position to the extended position by moving the stop from the recess into the slot.

In an embodiment, movement of the locking member from the second orientation to the third orientation by the actuator pushes the stop into the slot which permits the shield to move from the initial position to the extended position. Therefore, the shield can be allowed to move into the extended position by depressing of the actuator.

The stop may be coupled to a resilient member that is configured to bend in order to move the stop inwards from a resting state towards the longitudinal axis of the trainer into a flexed state. The stop in the resting state holds the shield in the initial position. The stop in the flexed state permits the stop to move into the slot. This provides a reliable mechanism for allowing the shield to move from the initial position to the extended position.

The trainer may comprise a biasing element that biases the shield to move distally. Thus, the shield can move automatically from the retracted position to either the initial position or the extended position, depending on the orientation of the locking member.

The actuator resistance surface of the locking member may comprise a deflector portion. The actuator may be arranged to interface with the deflector portion to move the locking member from the second orientation to the third orientation. Therefore, the actuator pushes down on the deflector portion in order to move the locking member into the orientation that permits the shield to move to the extended position.

The trainer may comprise a biasing element arranged to bias the locking member in a first rotational direction. The biasing element may comprise a torsion spring. The biasing element may bias the locking member to rotate away from the second orientation or the third orientation towards the first orientation. Therefore, it is possible to automatically reset the trainer.

The biasing element may bias the locking member towards a fourth orientation such that once the actuator has moved a distance towards the distal position and the shield is in the extended position the locking member moves into the fourth orientation. The locking member in the fourth orientation may prevent the shield from moving from the extended to position to the initial position. Therefore, the shield can automatically be positioned in a locked-out state, once the actuator has been depressed.

The actuator may be configured to interfere with the locking member when moving from the distal position to the proximal position to move the locking member towards the first orientation thus allowing the shield to move from the extended position to the initial position. This allows the user to reset the trainer by moving the actuator back to the proximal position from the distal position.

The locking member may comprise a shield resistance surface that is arranged to resist proximal movement of the shield when the locking member is in the fourth orientation and the shield is in the extended position. The shield may comprise an abutment surface that abuts the shield resistance surface when the locking member is in the fourth orientation and the shield is in the extended position. This assists in maintaining the shield in the locked-out state.

In an embodiment, the proximal position of the actuator simulates an unactivated position of a plunger of an injection device. In an embodiment, the distal position of the actuator simulates an activated position of a plunger of an injection device. In an embodiment, the initial position of the shield simulates covering of a needle of an injection device. In an embodiment, the retracted position of the shield simulates exposing a needle of an injection device. In an embodiment, the extended position of the shield simulates a locked-out state of an injection device in which the shield is prevented from exposing a needle. Therefore, the trainer can accurately simulate the operation of an injection device.

The latch may be configured such that an audible sound is emitted when the latch couples with the body protrusion, thus indicating that the actuator is in the distal position. The audible sound indicates that the actuator has reached the distal position which simulates completion of an injection being administering by an injection device so that the user can more accurately determine that an injection has been administered properly when using the injection device.

The latch may be configured to hold the actuator in the distal position when the latch is coupled with the body protrusion. Coupling of the latch to the body protrusion indicates that the actuator has reached the distal position which simulates completion of an injection being administering by an injection device so that the user can more accurately determine that an injection has been administered properly when using the injection device.

The latch may comprise a resilient member. The latch may be moveable between an uncoupled state in which the latch is not coupled with the body protrusion and a coupled state in which the latch is coupled with the body protrusion. Therefore, the latch simply can be bent into coupling with the body portion.

The resilient member may be arranged to move from the coupled state to the uncoupled state when a force above a threshold is applied to the actuator in moving the actuator from the distal position to the proximal position. Therefore, the latch can hold the actuator in the distal position securely, while allowing the trainer to return to its initial configuration when a user purposefully applies a force above the threshold to the actuator.

The latch may comprise a latch deflector portion that is arranged to interface with the body protrusion in order to move the latch from the uncoupled state into the coupled state. The latch may comprise a gripping element that grips the body portion in the coupled state. In this way, the deflector portion assists in moving the latch into coupling with the body, and the gripping element assists in maintain the latch and body in connection with one another.

The resilient member may comprise the deflector portion and/or the gripping element. The deflector portion and the gripping element may be provided on opposite sides of the latch. This provides a reliable construction for the latch.

The connector may resist the shield from moving distally away from the initial position when the actuator is in the proximal position. In this way, the connector assists in maintaining the shield in the initial position.

The connector may allow the shield to move towards the retracted position when the actuator is in the proximal position. In this way, the connector does not impede retraction of the shield to the retracted position.

The connector may allow the shield to move distally towards the extended position when the actuator moves towards the distal position. Thus, the connector can act to release the shield.

The connector may have an actuator interface that abuts a portion of the actuator to resist the shield from moving distally away from the initial position when the actuator is in the proximal position. The abutment of the actuator interface and the actuator provides a mechanism for holding the shield in the initial position.

The actuator interface may abut a surface of the actuator that faces the proximal direction. Thus, the connector can be moved by the actuator when the actuator moves proximally, but the actuator does not move the connector when it moves distally.

The connector may have a shield interface that abuts a portion of the shield to resist the shield from moving distally away from the initial position when the actuator is in the proximal position. This provides a mechanism for holding the shield in the initial position.

The shield interface may abut a surface of the shield that faces the distal direction. Thus, the connector can move the shield when the actuator moves proximally, but the connector does not move the shield when it moves distally.

In another aspect of the invention, there is a kit of parts configured for assembly into an injection device trainer or an injection device as described herein.

BRIEF DESCRIPTION OF THE DRAWINGS

Embodiments of the invention will be described, by way of example, with reference to the following drawings, in which:

FIG. 2C illustrates the actuator in the proximal position and the shield in a retracted position;

FIG. 2D illustrates the actuator moved distally from the proximal position and the shield in the retracted position;

FIG. 2E illustrates the actuator in a distal position and the shield in the retracted position;

FIG. 3A illustrates the actuator in the distal position and the shield in an extended position;

FIG. 3B illustrates the actuator as it moves proximally towards distal position and the shield in an extended position;

FIG. 3C illustrates the actuator in the distal position and the shield in the initial position;

DETAILED DESCRIPTION

Figure 1:
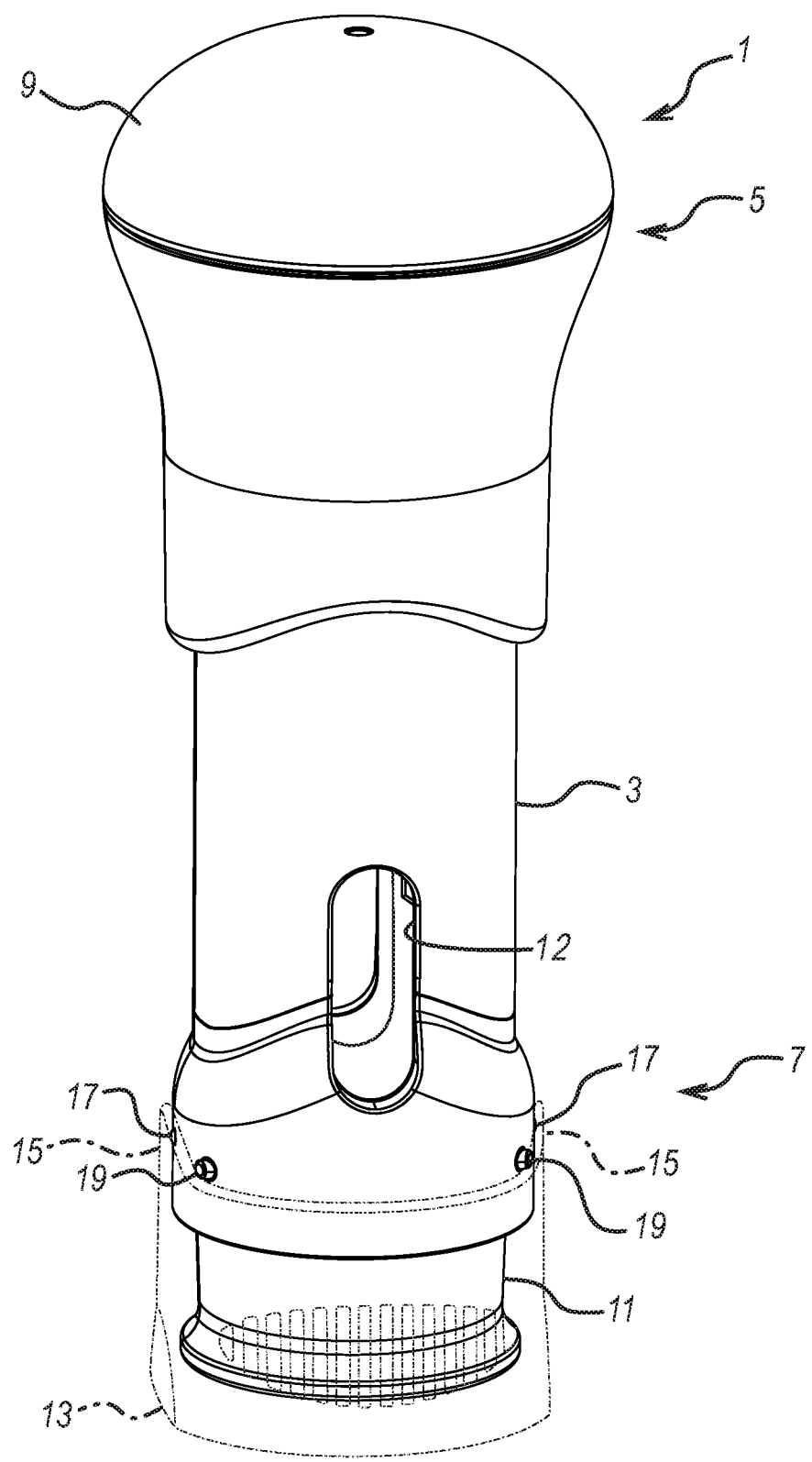
FIG. 1 illustrates an injection device trainer for training a user to use an injection device.

Referring to FIG. 1, there is an injection device trainer 1 for training a user to use an injection device. The trainer 1 comprises a body portion 3 which has a proximal end 5 and a distal end 7.

In use, the distal end 7 of the body portion 3 is positioned towards a surface of the user's body, which may be a target site into which the user would normally administer an injection. In use, the proximal end 5 of the body portion 3 is positioned towards the user's hand that is used to activate the trainer 1. The body portion 3 also has a window 12 in each side of the body portion 3 which simulates a window in an injection device that is used to view the medicament contained within the device.

Although the terms "proximal" and "distal" are used herein to describe the device, these terms are used to provide context and do not require the trainer 1 to be used in any particular orientation. The terms "first end" and "second end" could be used in place of the terms "distal end" and "proximal end" without changing the intended meaning.

The injection device trainer 1 also comprises an actuator 9 and a shield 11. The actuator 9 simulates the plunger in an injection device that is used to dispense medicament from a needle. The shield 11 simulates the needle shield in an injection device that is used to cover and expose the needle.

The trainer 1 has a removable cap 13 that can be positioned over the shield 11 in order to prevent accidental retraction of the shield 11. The cap 13 comprises a pair of indents 15 on its inner surface. These indents 15 are arranged to be positioned over a pair of raised portions 17 on an outer surface of the distal end 7 of the body portion 3. This holds the cap 13 in place. The distal end 7 of the body portion 3 also comprises a pair of nodes 19 on opposite sides of each indent 15 that abut with the surface of the shield 11, so that the shield 11 is prevented from progressing further towards the proximal end 5 once the indents 15 have interfaced with the raised portions 17.

The features of the injection device trainer 1 described herein may be identical or substantially identical to those of the injection device on which the user is to be trained. However, the injection device trainer 1 does not comprise a needle so that a user is not injected during the training procedure. The injection device trainer 1 also does not comprise any fluid, such as a medicament, contained within it, although the trainer 1 may comprise a container that simulates the vessel for containing the medicament of the injection device.

Figure 2A:
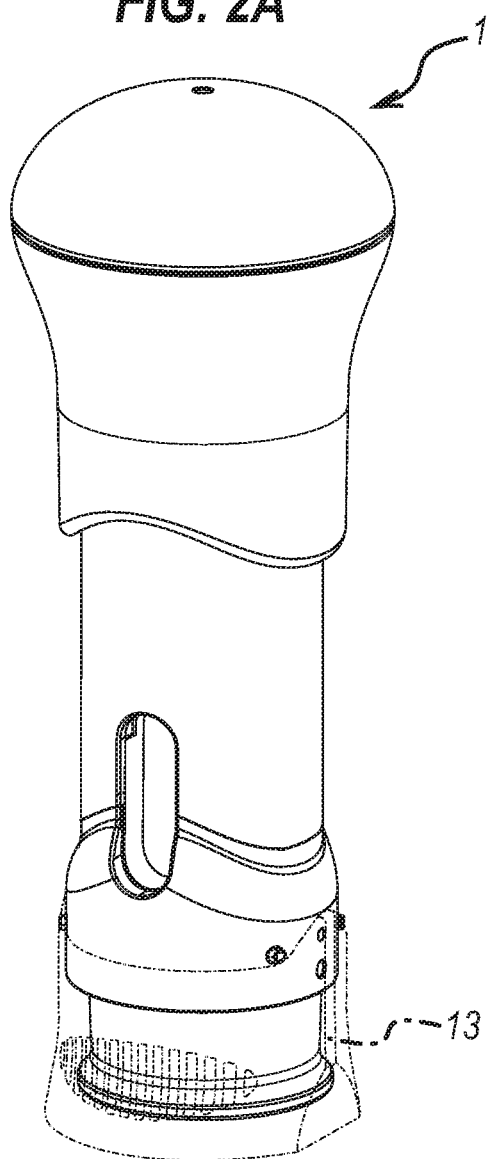
FIG. 2A illustrates a cap attached to a distal end of the injection device trainer.
Figure 2B:
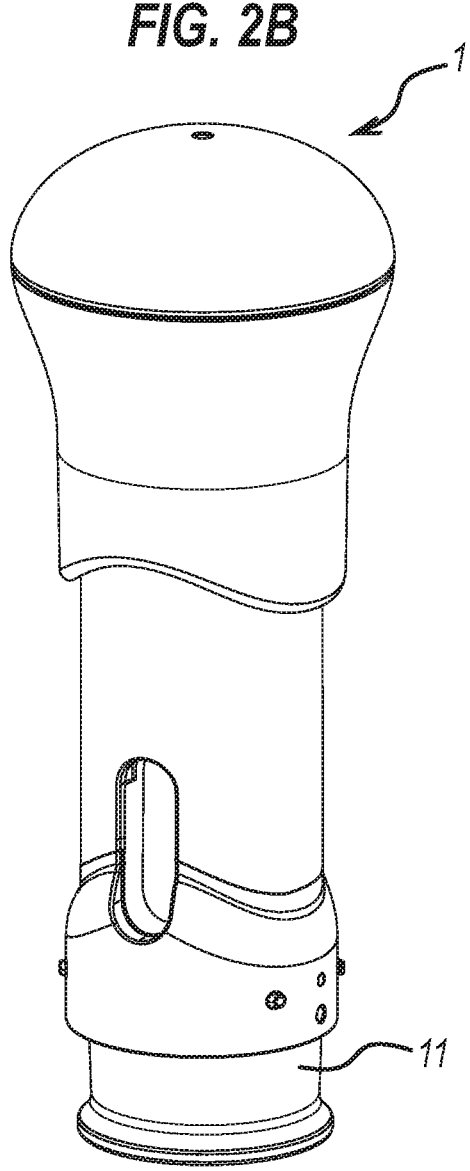
FIG. 2B illustrates the injection device trainer with an actuator in a proximal position and a shield in an initial position.

Referring to FIGS. 2A-E, there is a sequence for training a user on administering an injection using the injection device trainer 1. As can be seen, FIG. 2A represents the trainer 1 as described with reference to FIG. 1. FIG. 2B illustrates the trainer 1 with the cap 13 removed which exposes the shield 11. As shown in FIG. 2B, the shield 11 is in an initial position which simulates the position of a needle shield of an injection device in which the needle is covered.

Referring to FIG. 2C, the user can grip the trainer 1 by the actuator 9 and position the shield 11 over the target site. Then, the user can push the actuator 9 towards the distal end 7 of the body portion 3. This action causes the shield 11 to move in the direction of the proximal end 5 to a retracted position of the shield 11. The actuator 9 is prevented from moving towards the distal end 7 relative to the body portion 3, when the shield 11 is in the initial position. Therefore, the actuator 9 is held in a proximal position and cannot advance forward. However, once the shield 11 is in the retracted the position, the actuator 9 is allowed to move in the distal direction along the longitudinal axis of the trainer 1.

FIG. 2C illustrates the shield 11 in the retracted position which is a position more proximal relative to the body portion 3 than the initial position. The shield 11 is partially retracted inside the body portion 3 when in the retracted position. This position simulates the position of a needle shield of an injection device in which the needle is exposed for administering an injection.

Referring to FIGS. 2D and 2E, the actuator 9 is allowed to move distally once the shield 11 is in the retracted position. FIG. 2D illustrates the actuator 9 progressing towards the distal end 7. FIG. 2E illustrates the actuator 9 in a distal position which simulates the position of the plunger in an injection device once the injection has been administered.

Referring to FIGS. 3A-C, there is a sequence for resetting the injection device trainer 1 once simulation of an injection has been completed. Referring to FIG. 3A, the user can remove the trainer 1 from the target site which permits the shield 11 to move distally to an extended position that is more distal relative to the body portion 3 than the initial position and the retracted position. The extended position of the shield 11 simulates a locked-out state of an injection device in which a needle shield of the injection device is prevented from exposing a needle.

Referring to FIGS. 3B-C, the user can pull the actuator 9 towards the proximal end 5 in order to reset the trainer 1 so that the sequence described with reference to FIGS. 2A-E can be repeated. FIG. 3B illustrates the actuator 9 progressing towards the proximal position, and FIG. 3C illustrates the actuator 9 once it has reached the proximal position. When the actuator 9 is pulled into the proximal position, this causes the shield 11 to return to the initial position so that the trainer 1 can be used for another instance of training.

Figure 4:
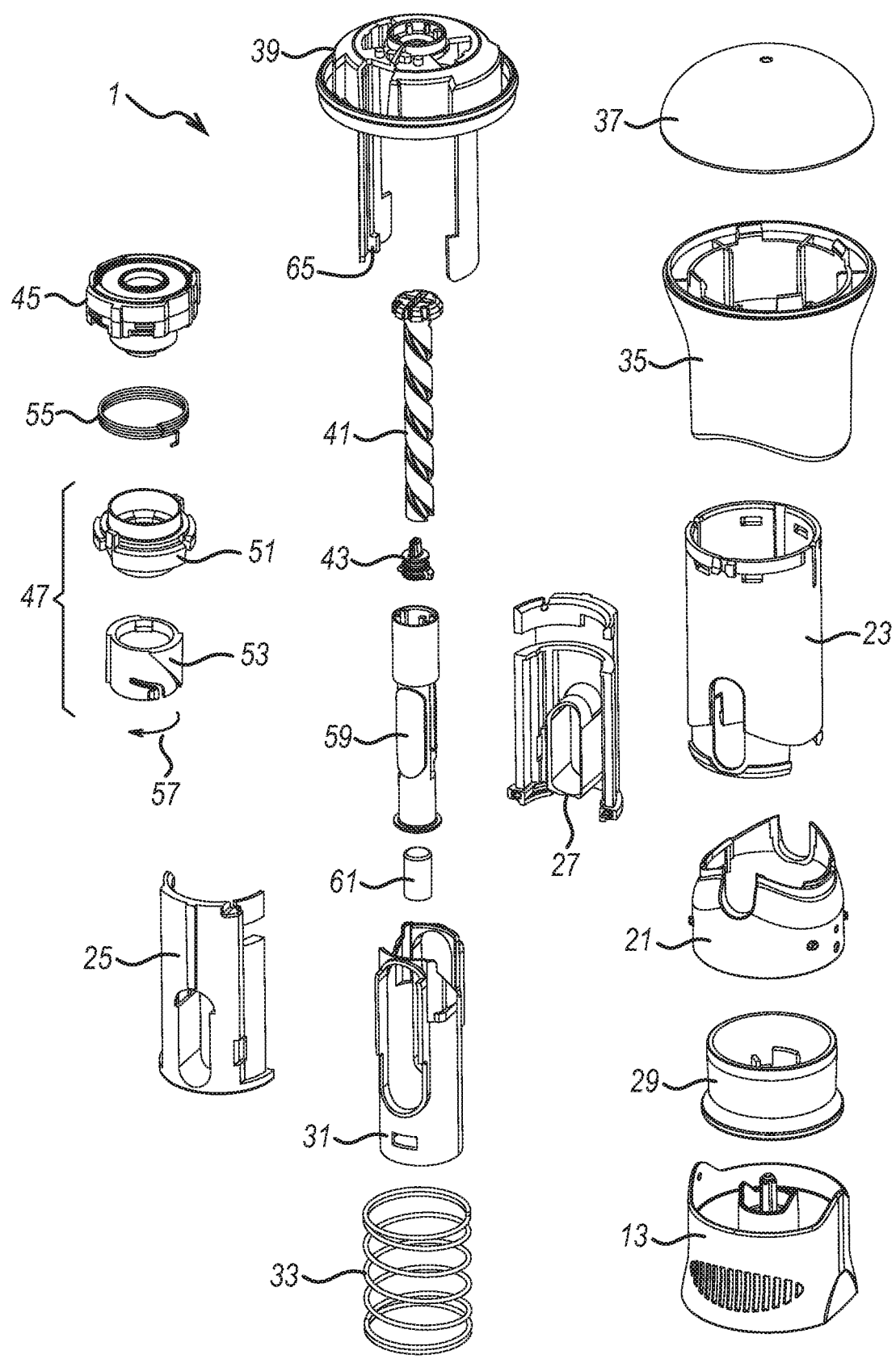
FIG. 4 illustrates an exploded view of the injection device trainer.

FIG. 4 illustrates an exploded view on the injection device trainer 1. The body portion 3 comprises a base portion 21 that connects with a main portion 23 which is encased by a first outer portion 25 and a second outer portion 27. In this example, the component parts of the body portion 3 fit together in order to form a body assembly. However, the body portion 3 could be formed of a single piece.

The shield 11 of the trainer 1 comprises an outer shield portion 29 and an inner shield portion 31. The outer shield portion 29 extends from the base portion 21 while the inner shield portion 31 sits within the body portion 3. There is also a spring 33 which acts as a biasing element for urging the shield 11 in the distal direction.

The actuator 9 of the trainer 1 comprises an actuator body 35 and an end cap 37. These components form an external surface with which the user can interact in order to move the actuator 9. There is an inner piece 39 of the actuator 9 that sits within the actuator body 35 and the end cap 37. The inner piece 39 connects with a threaded plunger 41 at a proximal end of the plunger 41, while a distal end of the plunger 41 connects with a tip 43 that maintains the plunger 41 in alignment with the longitudinal axis of the trainer 1. In this example, the component parts of the actuator 9 fit together in order to form an actuator assembly. However, the actuator 9 could be formed of a single piece.

The plunger 41 is coupled with damping element 45 that is used to damp the rotation of the plunger 41 which, in turn, damps movement of the actuator 9 towards the distal position.

The trainer 1 further comprises a locking member 47 comprising a first locking portion 51 and a second locking portion 53. In this example, the first and second locking portions 51, 53 are separate components that connect together to form the locking member 47. However, in another example the locking member 47 is formed from a single piece.

The locking member 47 is rotatable about the longitudinal axis of the trainer 1 such that the locking member 47 can be placed in different rotational orientations. The locking member 47 can rotate but cannot move proximally or distally with respect to the body portion 3. The locking member 47 has a first orientation in which the locking member 47 resists movement of the actuator 9 from its proximal position (as shown in the FIGS. 2A-B) to the distal position (as shown in FIG. 2E). Therefore, the first orientation of the locking member 47 is configured to hold the actuator 9 in the configuration described with reference to FIGS. 2A-B. Also, the first orientation of the locking member 47 is configured to hold the shield 11 in the initial position (as shown in FIG. 2B) such that the shield 11 is prevented from moving from the initial position to the extended position (as shown in FIGS. 3A-B), and permits movement of the shield 11 from the initial position to the retracted position (as shown in FIG. 2C).

The locking member 47 also has a second orientation in which the locking member 47 permits the actuator 9 to move from the proximal position to the distal position. Therefore, the second orientation of the locking member 47 is configured to allow the actuator 9 to move into the position illustrated in FIG. 2E.

The trainer 1 also comprises a biasing element 55, which in this example is a torsion spring. The biasing element 55 biases the locking member 47 in a first rotational direction 57. The first rotation direction 57 may be clockwise or anticlockwise depending on the orientation of the trainer 1.

The trainer 1 further comprises an inner housing 59 that simulates a syringe of an injection device, and a grip 61 that holds the inner housing in place.

Figure 5A:
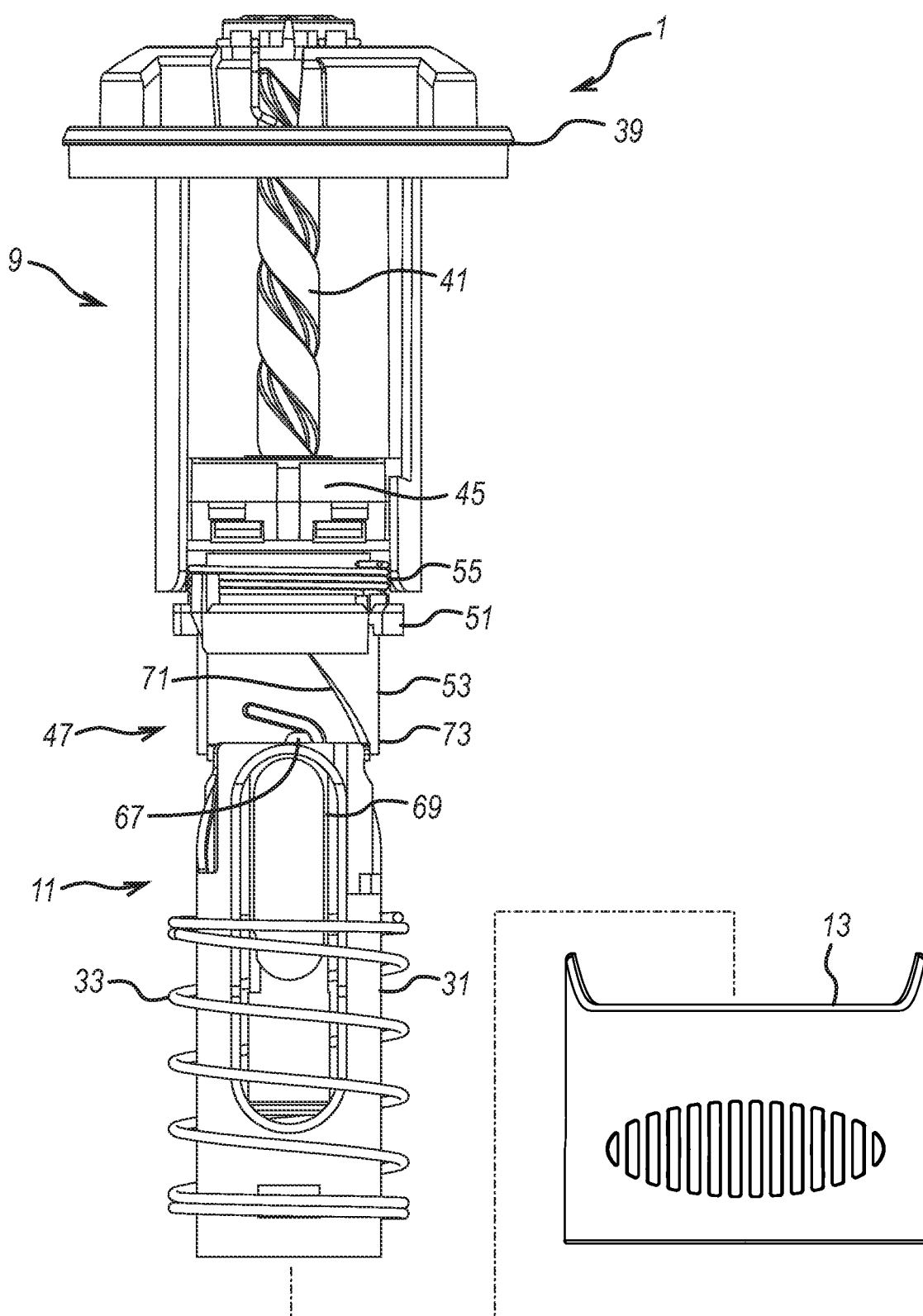
FIG. 5A illustrates a side view of internal components of the injection device trainer with the actuator in the proximal position and the shield in the initial position.
Figure 5B:
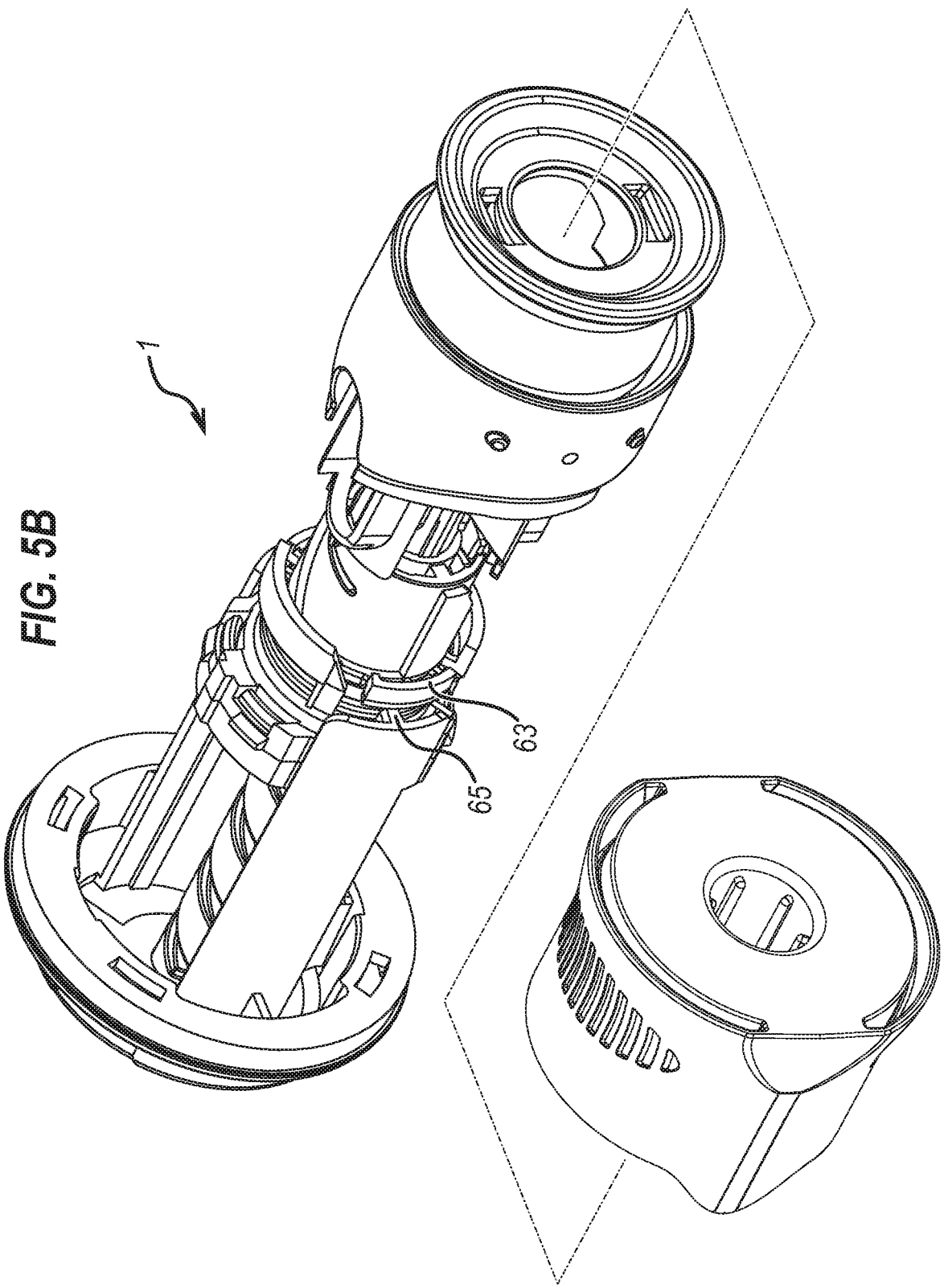
FIG. 5B illustrates a perspective view of internal components of the injection device trainer with the actuator in the proximal position and the shield in the initial position.

FIGS. 5A-B illustrate the trainer 1 in the same configuration as described with reference to FIGS. 2A-2B with the actuator 9 in the proximal position and the shield 11 in the initial position. In this configuration the locking member 47 is in the first orientation which prevents the actuator 9 moving in the distal direction.

Figure 6:
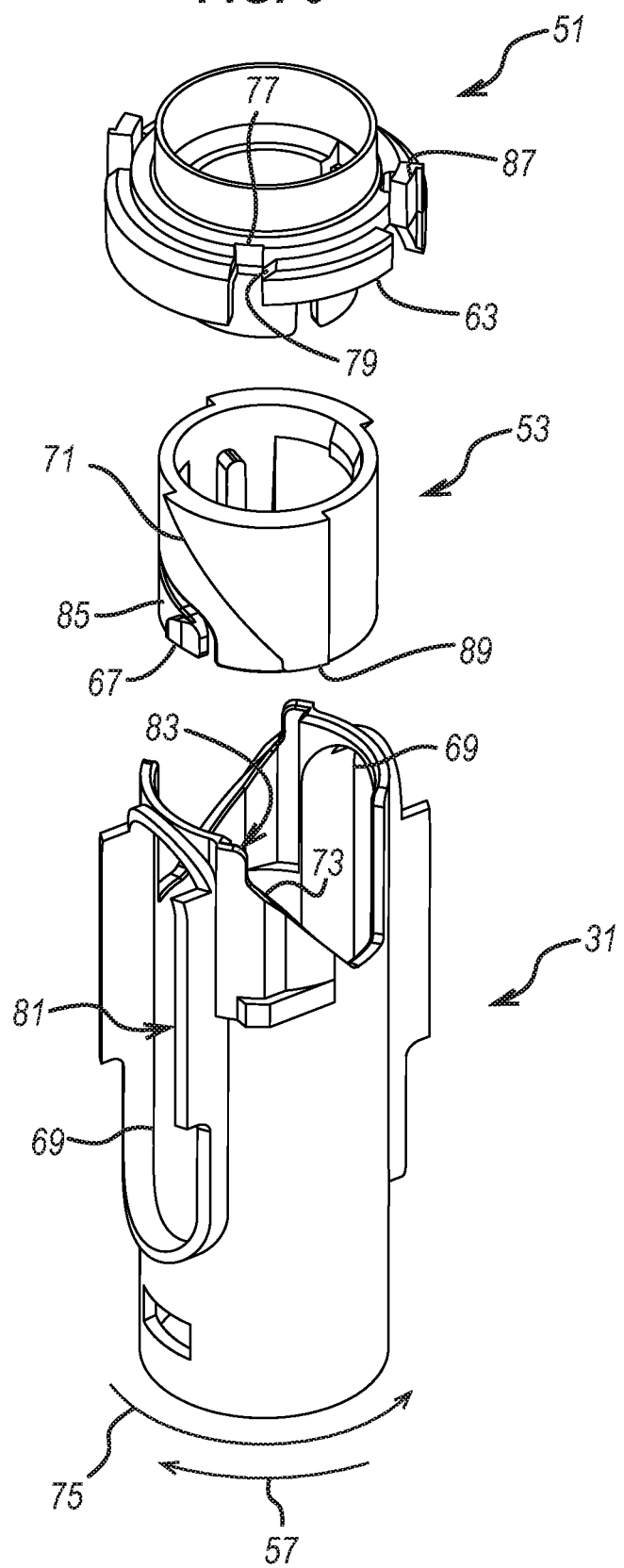
FIG. 6 illustrates an exploded view of an inner shield portion and a locking member.

Referring to FIGS. 5A-B and FIG. 6, the locking member 47 comprises an actuator resistance surface 63 which comprises a protrusion that protrudes from a part of the outside surface of the cylindrical housing of the locking member 47. The actuator resistance surface 63 protrudes from the locking member 47 in a direction away from the longitudinal axis of the trainer 1. The actuator 9 comprises an abutment surface 65 which comprises a protrusion that protrudes from a part of the inside surface of the actuator 9. The abutment surface 65 protrudes from the actuator 9 in a direction towards the longitudinal axis of the trainer 1. The abutment surface 65 is arranged to abut against the actuator resistance surface 63. Therefore, the actuator resistance surface 63 is arranged to resist movement of the actuator 9 from the proximal position to the distal position when the locking member 47 is in the first orientation.

In the trainer 1 there are two actuator resistance surfaces 63. In this example, the actuator resistance surfaces 63 are positioned on opposite sides of the locking member 47 to one another. This allows the force of the actuator 9 being pressed down to be spread across the locking member 47. There are also two corresponding abutment surfaces 65, which in this example, are positioned on opposite sides of the actuator 9 to one another.

The locking member 47 comprises a stop 67 that is arranged to sit within a recess 69 in the inner shield portion 31 of the shield 11. The stop 67 prevents the shield 11 from moving distally from the initial position to the extended position, but permits the shield 11 to move proximally towards the retracted position. In this example, the locking member 47 comprises a pair of stops 67 positioned on opposite sides of the locking member 47 to one another. The inner shield portion 31 comprises a pair of corresponding recesses 69 on opposite sides of the inner shield portion 31 to one another. The recesses 69 define an aperture with similar, or the same, dimensions as the window 12 described with reference to FIG. 1.

Figure 7A:
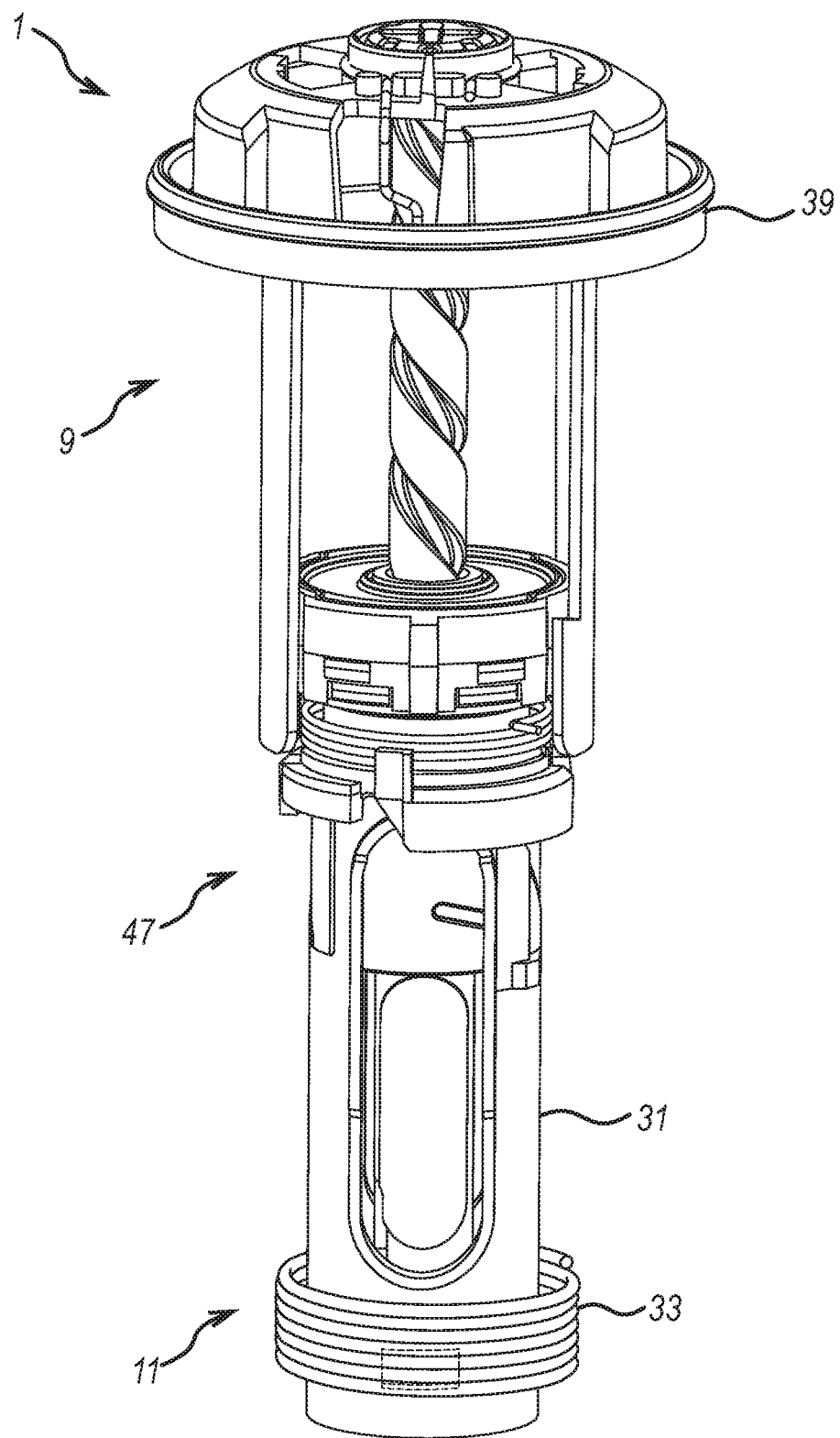
FIG. 7A illustrates a side view of internal components of the injection device trainer with the actuator in the proximal position and the shield in the retracted position.
Figure 7B:
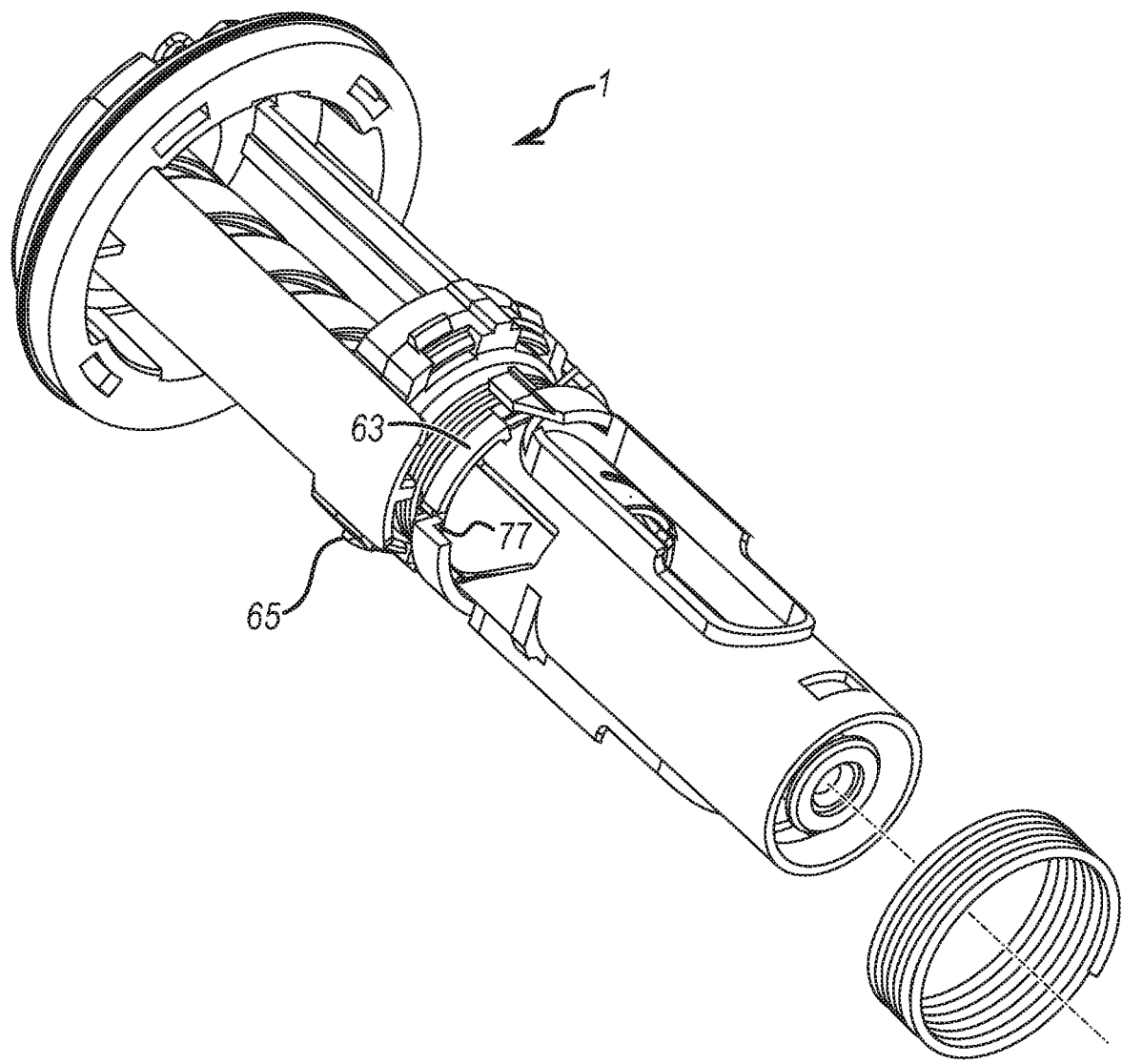
FIG. 7B illustrates a perspective view of internal components of the injection device trainer with the actuator in the proximal position and the shield in the retracted position.

FIGS. 7A-B illustrate the trainer 1 in the same configuration as described with reference to FIG. 2C with the actuator 9 in the proximal position and the shield 11 in the retracted position. In this configuration the locking member 47 has been rotated into the second orientation which permits the actuator 9 to move in the distal direction, as is described in more detail below.

Referring to FIGS. 5A and 6, the locking member 47 comprises a ramp 71 which in this example is an angled surface that extends from the outside surface of the second locking to portion 53. The inner shield portion 31 comprises a ramp interface 73 which in this example is an angled surface in a recess in the inner shield portion 31. The ramp 71 and the ramp interface 73 are shaped and positioned such that when the shield 11 is moved from the initial position to the retracted position the ramp interface 73 causes the locking member 47 to rotate. In this example, the ramp 71 and ramp interface 73 cause the locking member 47 to rotate in a second rotational direction 75 which is the opposite rotational direction to the first rotational direction 57 towards which the locking member 47 is biased.

Preferably, the locking member 47 comprises a pair of ramps 71 and the shield 11 comprises two ramp interfaces 73. Each ramp 71 may be on an opposite side of the locking member 47 to the other. Each ramp interface 73 may be on an opposite side of shield 11 to the other. This assists in reducing the frictional forces on the locking member 47 and the shield 11.

Movement of the shield 11 into the retracted position causes the locking member 47 to rotate into the second orientation, which is illustrated in FIGS. 7A-B. Here it can be seen that the protrusion formed by the ramp 71 fits inside the recess formed by the ramp interface 73 in order to hold the shield 11 in the retracted position. When the locking member 47 is in the second orientation, a gap 77 formed at an end of the actuator resistance surface 63 is at least partially rotationally aligned with the abutment surface 65, such that the abutment surface 65 can pass through the gap 77. Therefore, the abutment surface 65 can move past the actuator resistance surface 63, and the actuator 9 can begin to move from the proximal position towards the distal position. The width of the abutment surface 65 is the same as or less than the width of the gap 65. In the example, where there are two abutment surfaces 65 and two actuator resistance surfaces 63, the same process as described above occurs on the opposite sides of the trainer 1.

Referring to FIG. 6, the actuator resistance surface 63 of the locking member 47 comprises a deflector portion 79 that is configured to interface with the abutment surface 65 of the actuator when the actuator moves distally. When the abutment surface 65 interfaces with the deflector portion 79, this causes the locking member 47 to move further in the second rotational direction 75 from the second orientation to a third orientation. As the actuator 9 moves a first distance in the distal direction, the abutment surface 65 moves to sit inside the gap 77 in the locking member 47. Therefore, the force of the actuator 9 moves the locking member 47 into the third orientation, which moves the stop 67 into a slot 81 in the inner surface of the inner shield portion 31. When the abutment surface 65 sits within the gap 77, this holds the locking member 47 in the third orientation. The abutment surface 65 does not extend to the top of the actuator 9. Therefore, once the abutment surface 65 has moved past the gap 77 and the shield 11 has moved out of the engagement with locking member 47, it is possible for the locking member 47 to rotate back in the first rotational direction due to the force applied by the biasing element 55.

The slot 81 in the inner shield portion 31 forms a track within which the stop 67 can slide. The slot 81 has an opening 83 at a proximal end of the inner shield portion 31. The slot 81 permits the shield 11 to move in the distal direction from the retracted position towards the extended position, and once the stop 67 reaches the opening 83 the inner shield portion 31 is released from contact with the locking member 47.

The shield 11 is allowed to move into the extended position when the stop 67 exits the opening 83 of the slot 81. This permits the shield 11 to move past the locking member 47 to the extended position, which is more distal than the position of the locking member 47 and more distal than the initial position. The location of the shield 11 relative to the locking member 47 when the shield 11 is in the extended position is shown in FIG. 8, which is the configuration described with reference to FIG. 3A.

Referring to FIG. 6, the stop 67 comprises a resilient member 85 that is configured to be flexed inwards by the inner shield portion 31. Thus, the resilient member 85 and the stop 67 can move inwards towards the longitudinal axis of the trainer 1. The stop 67 is forced against an edge of the recess 69 when the actuator 9 forces the locking member 47 to rotate from the second orientation to the third orientation. This pushes the stop 67 and the resilient member 85 inwards, so that the stop 67 can enter the slot 81 in the inner shield portion 31. As illustrated, the stop 67 has an angled surface, which assists in flexing the resilient member 85 inwards.

Figure 8:
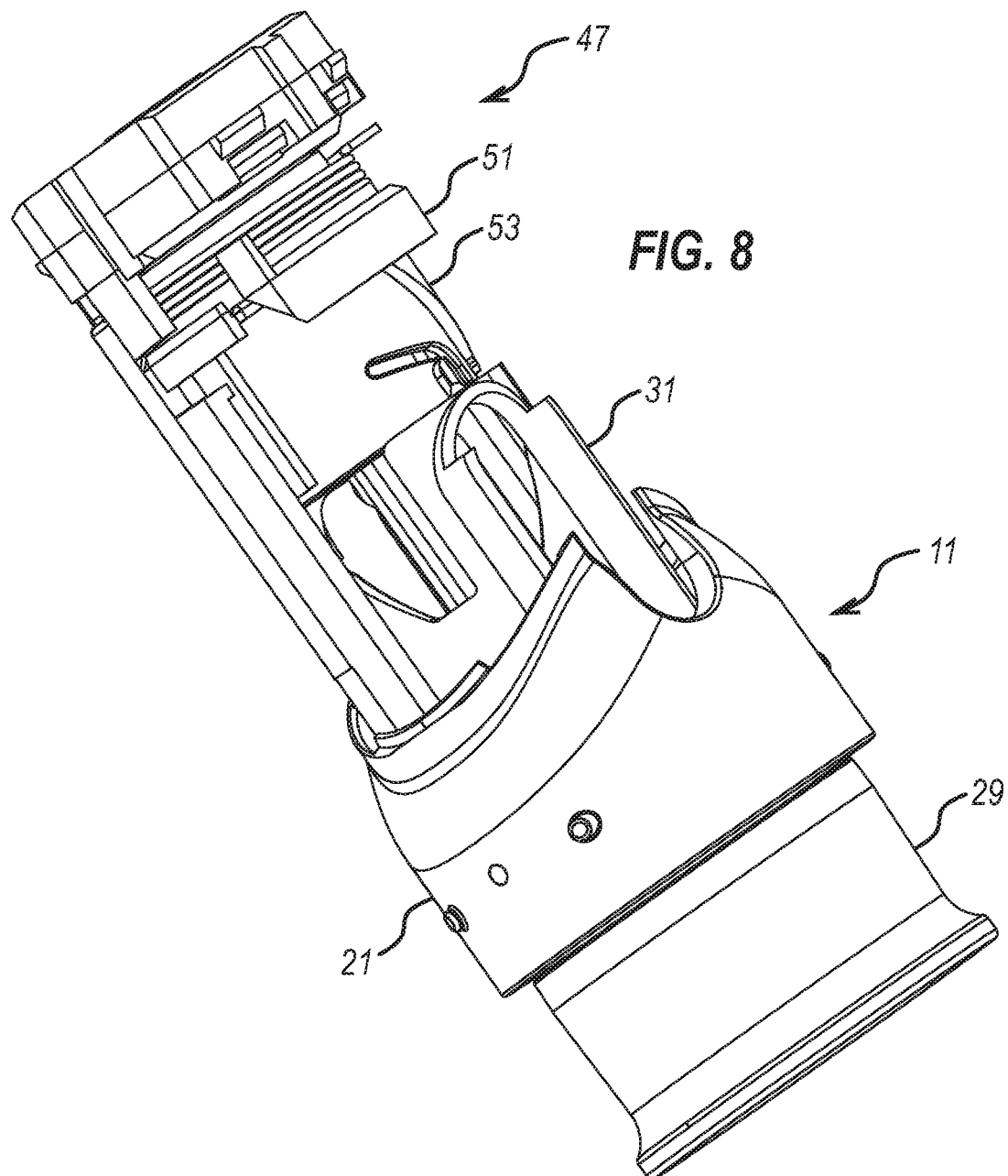
FIG. 8 illustrates a perspective view of internal components of the injection device trainer with the actuator in the distal position and the shield in the extended position.

When the trainer 1 is in the state illustrated in FIG. 3A and FIG. 8, the actuator 9 no longer holds the locking member 47 in the third orientation, and the ramp 71 can no longer touch the ramp interface 73. Therefore, the locking member 47 is free to rotate in the first rotational direction 57, and is urged in this direction by the biasing element 55.

The locking member 47 rotates past the first orientation and into a fourth orientation in which a portion of the actuator 9 abuts a reset deflector 87 on the locking member 47. This holds the locking member 47 in the fourth orientation, which prevents the shield 11 from moving proximally from the extended position towards the initial position. Therefore, the shield 11 simulated a locked-out state of an injection device.

When the locking mechanism 47 is in the fourth orientation, a shield resistance surface 89 abuts against a surface on the proximal end of the inner shield portion 31. In this example, the shield resistance surface 89 is a protrusion extending from the ramp 71. The shield resistance surface 89 blocks the path of the shield 11, so that it cannot move proximally from the extended position.

As described above with reference to FIGS. 3A-C, the user can reset the trainer 1 by pulling the actuator 9 from the distal position back to the proximal position. When the actuator 9 moves in the proximal direction the abutment surface 65 interfaces with an angled surface of the reset deflector 87 in order to rotate the locking mechanism 47 from the fourth orientation into the first orientation.

When the locking member 47 has rotated by a first angular distance in the second rotational direction 75 towards the first orientation, the shield resistance surface 89 is no longer directly above the proximal end of the inner shield portion 31 in the direction of the longitudinal axis of the trainer 1. Instead, the shield resistance surface 89 is directly above a recess in the inner shield portion 31 in the direction of the longitudinal axis of the trainer 1. Therefore, the shield 11 is able to move towards the initial position from the extended position.

When the shield 11 is moved from the extended position back towards the initial position, the ramp interface 73 of the shield 11 exerts a force on the ramp 71 of the locking member 47. This causes the locking member 47 to move in the second rotational direction 75 towards the first orientation. As the inner shield portion 31 moves proximally, this forces the stop 67 and the resilient member 85 to flex inwards such that the stop 67 passes under the proximal end of the inner shield portion 31. As the inner shield portion 31 moves further, the stop 67 moves into the recess 69, which holds the shield 11 in the initial position as described above. In addition, once the shield 11 has reached the initial position, the locking member 47 has rotated into the first orientation as described above. Therefore, the trainer 1 can be reset back to the configuration described with reference to FIG. 2B.

Figure 9:
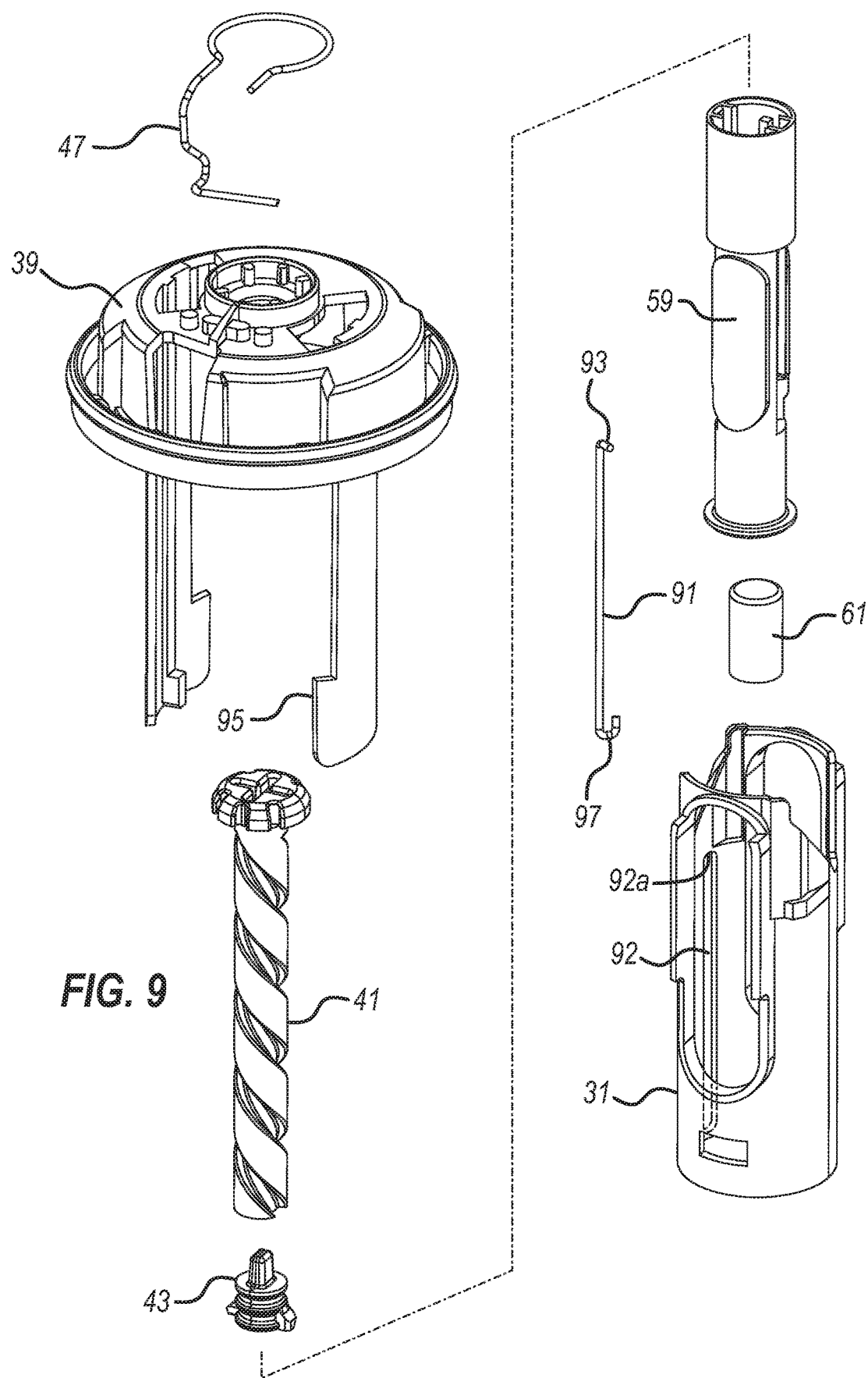
FIG. 9 illustrates an exploded view of the injection device trainer with a connector.

It is possible to move the shield 11 from the extended position in the direction of the initial position by hand in order to reset the device. However, this requires the user to move the actuator 9 into the proximal position at the same time as moving the shield 11 to the initial position in order to reset the device, thus requiring the use of two hands which is undesirable. Referring to FIG. 9, a reset connector 91 is provided that automatically pulls the shield 11 from the extended position into the initial position when the actuator 9 is pulled from the distal position into the proximal position.

The reset connector 91 is a rod of fixed length comprising an actuator interface, such as a first hook 93, at its proximal end. The first hook 93 is arranged to interface with a portion of the actuator 9, such as a ledge 95 on the inner piece 39 of the actuator 9. The ledge 95 faces in the proximal direction and therefore movement of the actuator in the proximal direction causes the reset connector 91 to move in the proximal direction when the ledge 95 contacts the first hook 93. However, movement of the actuator 9 in the distal direction does not force the reset connector 91 to move in this direction, since no force can be applied by the actuator 9 on the first hook 93 in this direction.

The rest connector 91 also comprises a shield interface, such as a second hook 97 at its distal end. The second hook 97 is arranged to abut with a portion of the shield 11, for instance by being received by an aperture 92 in the shield 11. When the reset connector 91 is moved in the proximal direction by the actuator moving towards the proximal position, a proximal end 92a of the aperture 92 contacts the second hook 97. This permits the reset connector 91 to pull the shield 11 toward the initial position in order to reset the trainer 1.

The aperture 92 may be configured, as illustrated by FIG. 9, as an elongated aperture extending distally along the inner shield portion 31. The second hook 97 may be positioned within the aperture at all times during operation of the trainer 1. In these embodiments, the second hook 97 tracks along the aperture 92 as the actuator 9 is moved distally from the proximal position, shown in FIG. 2B, to the distal position, shown in FIG. 2E, and moved proximally from the distal position towards the proximal position, until the second hook 97 contacts the proximal end 92a of the aperture, as described above, to permit the reset connector 91 to pull the shield 11 toward the initial position in order to reset the trainer 1.

The aperture 92 may be formed in any suitable part of the shield 11. For example, the aperture may be formed in the outer shield portion 29, and function in substantially the same manner as described above. The aperture 92 may extend, in a direction perpendicular to the longitudinal axis of the trainer 1, through the portion of the shield in which it is formed. Alternatively, the aperture may be an etched portion, or indent, in the surface of the shield 11.

In some embodiments, including that shown in FIG. 9, the aperture 92 may have a closed distal end. Alternatively, the aperture may be formed as a slot in the distal end of the inner and/or outer shield portion, having a closed, proximal end 92a against which the second hook 97 abuts, and an open distal end.

In some embodiments, the aperture may not extend along the shield 11 so distally that the second hook 97 is positioned within the aperture at all times during operation of the trainer 1. For example, the aperture 92 may be configured as an approximately circular aperture in the shield 11. The reset rod 91 may be configured such that the second hook 97 is resiliently biased into the aperture as the actuator is moved towards its proximal position, to permit contact between the second hook 97 and proximal end 92a of the aperture and, therefore, pulling of the shield 11 toward the initial position in order to reset the trainer 1. The second hook 97 may be shaped, at its distal end, to cam against a closed distal end of the aperture. When the reset rod 91 is moved in the distal direction by the actuator moving towards the distal position, camming between the second hook 97 and the distal end of the aperture overcomes the resilient biasing, allowing the second hook 97 to disengage the aperture 92 as the actuator is moved distally.

Figure 10:
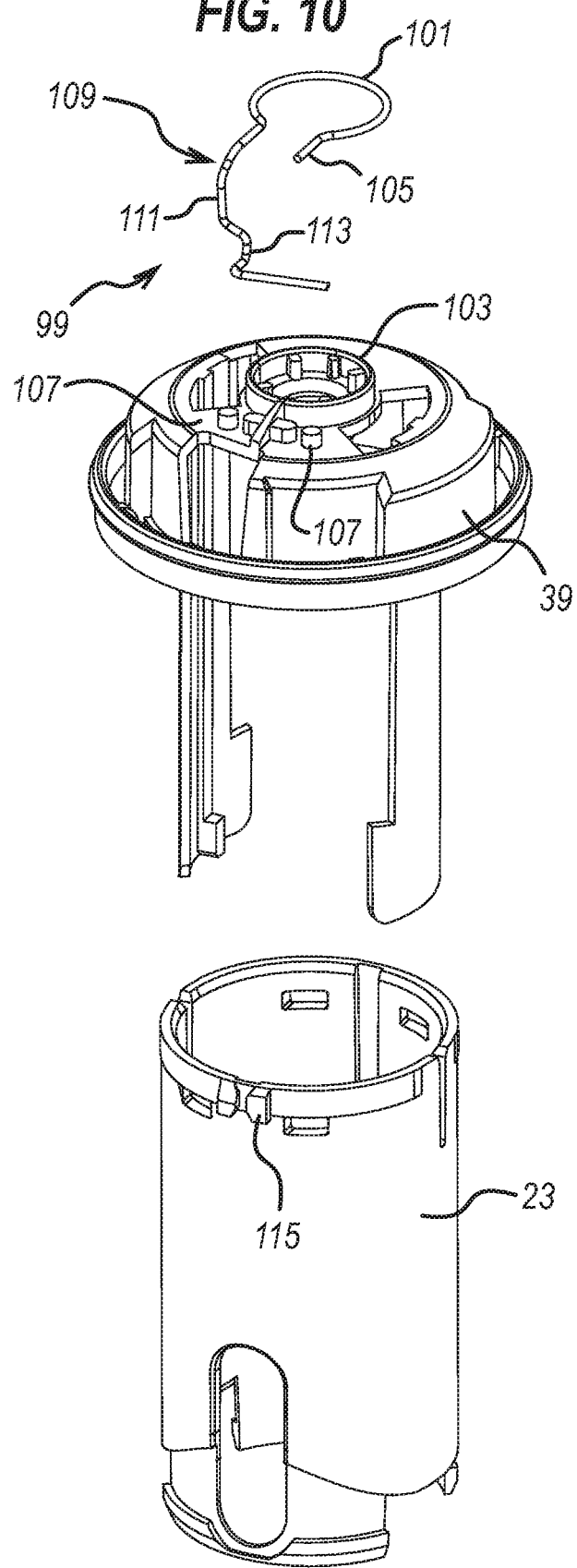
FIG. 10 illustrates an exploded view of the injection device trainer with a latch.

Referring to FIG. 10, the injection device trainer 1 comprises a latch 99 that is configured to attach to the inner piece 39 of the actuator 9. In this example, the latch 99 comprises a piece of resilient wire formed in a loop 101 that is arranged to be placed around a circular protrusion 103 on the inner piece 39. Since the latch 99 is resilient, the diameter of the loop 101 can be expanded to place it around the circular protrusion. Then, the loop can be released at which point the diameter of the loop 101 contracts so that the latch holds the circular protrusion 103. The latch 99 also comprises a first extension 105 that is configured to be located between a pair of holders 107 that hold the latch 99 in place.

The latch 99 further comprises a second extension 109 that in this example is longer than the first extension 105. The second extension 109 comprises a first portion 111 that extends in the distal direction and a second portion 113 that is angled with respect to the first portion 111. The second portion 113 forms a deflection portion on its distal side and gripping element on its proximal side. After the actuator 9 has moved a certain distance from the proximal position to the distal position, the second portion 113 comes into contact with a body protrusion 115 on the main portion 23 of the body portion 3.

As the actuator 9 moves distally, this causes the resilient latch 99 to bend outwardly away from the longitudinal axis of the trainer 1 and over the body protrusion 115. Once the actuator 9 has moved into the distal position, the latch 99 returns to its resting position. In this state, the angled surface of the latch 99, which represents the gripping element, couples the latch 99 to the body protrusion 115. This holds the actuator 9 in the distal position relative to the body portion 3

When the actuator 9 is moved from the distal position to the proximal position, the body protrusion 115 exerts force on the latch 99. When this force exceeds a threshold, the gripping element of the second portion 113 bends in a direction that is perpendicular to the direction that extends away from the longitudinal axis of the trainer 1. Thus, the gripping element passes by the body protrusion 115, so that the actuator 9 can be released from distal position. The threshold force required to bend the latch ensures that the actuator 9 is held securely in the distal position. However, the threshold force also permits the actuator 9 to snap back into the proximal position, once the gripping element releases the body protrusion.

Figure 11A:
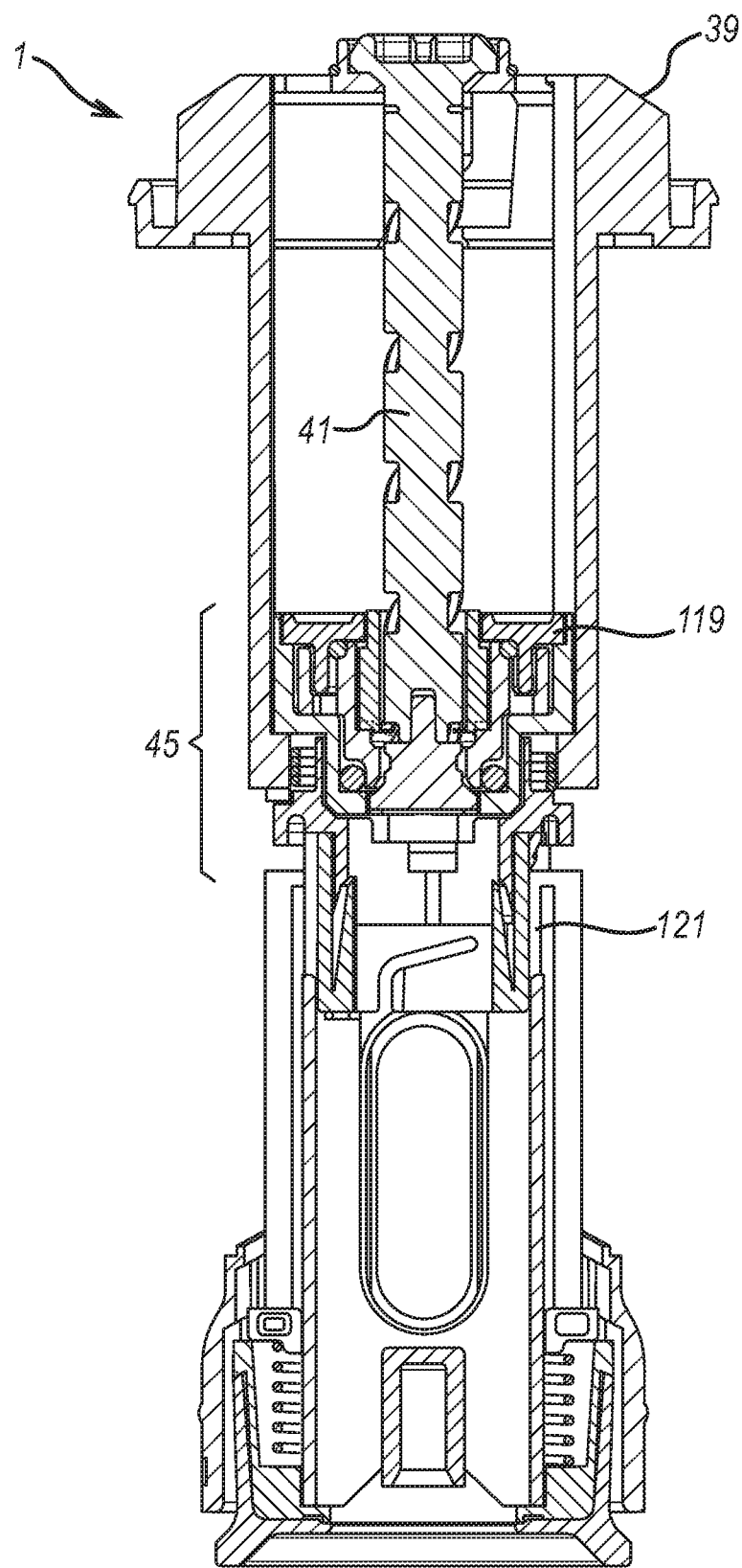
FIG. 11A illustrates a side view of internal components of the injection device trainer and damping element.
Figure 11B:
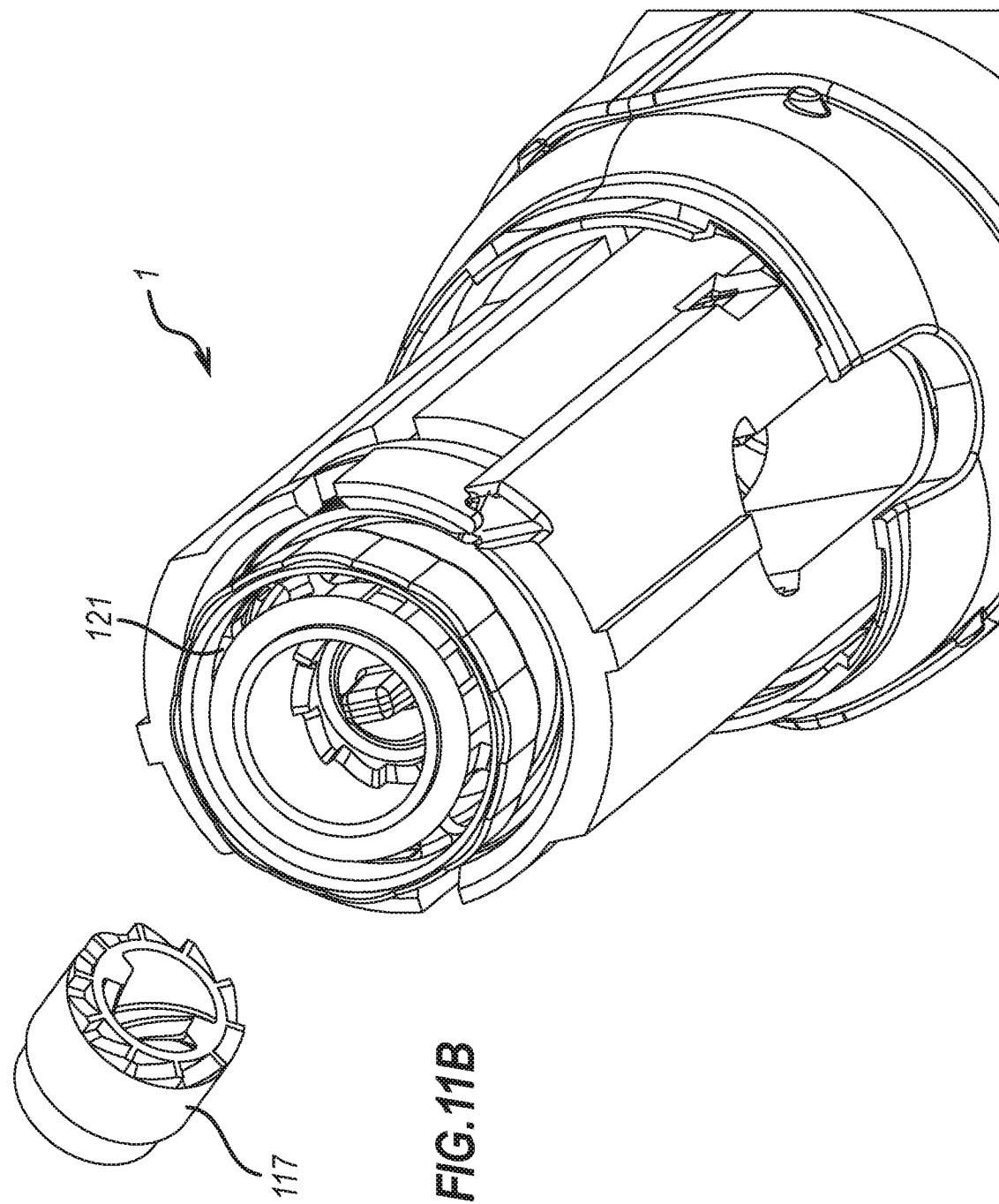
FIG. 11B illustrates a perspective view of internal components of the injection device trainer and damping element.
Figure 12A:
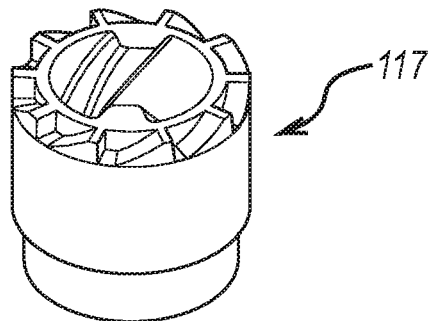
FIG. 12A illustrates a perspective view of the rotor.
Figure 12B:
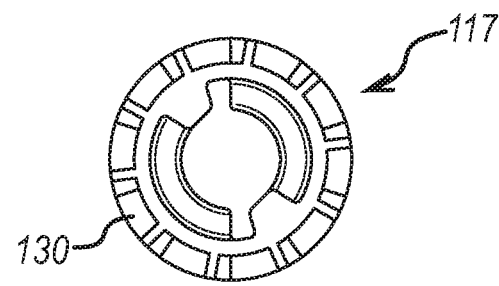
FIG. 12B illustrates a top view of the rotor, in which the angled teeth can be seen.
Figure 12C:
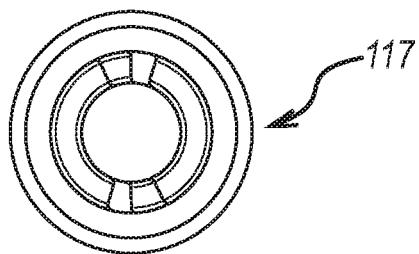
FIG. 12C illustrates a bottom view of the rotor.
Figure 13A:
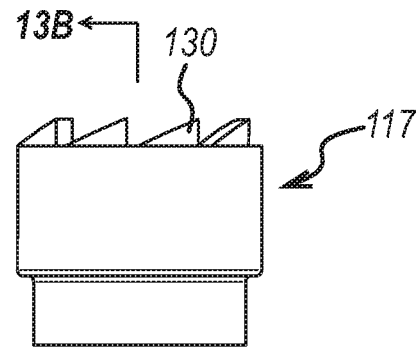
FIG. 13A illustrates a side view of the rotor.
Figure 13B:
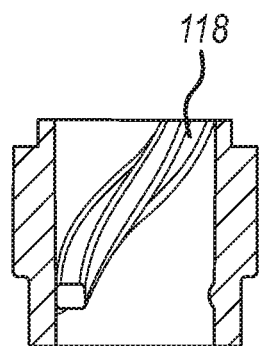
FIG. 13B illustrates a cutaway view taken along section A-A.
Figure 14A:
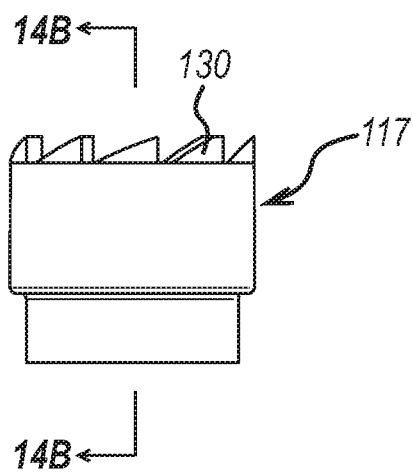
FIG. 14A illustrates a second side view of the rotor.
Figure 14B:
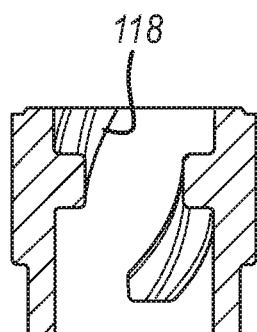
FIG. 14B illustrates a cutaway view taken along section B-B.
Figure 15:
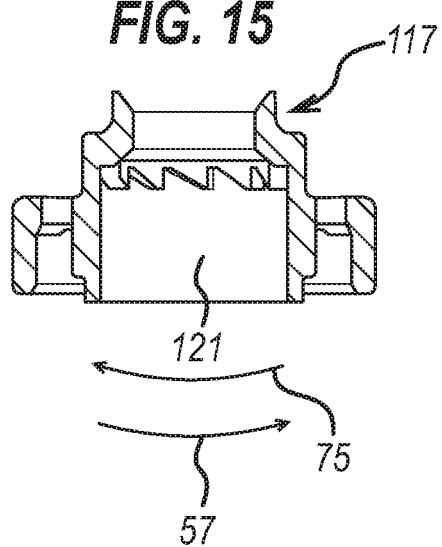
FIG. 15 illustrates a side view of the rotor and damping element, when fully engaged.

Referring to FIGS. 11A-B, the damping element 45 described briefly with reference to FIG. 4 is described in more detail below.

In the trainer 1, the plunger 41 of the actuator 9 has a thread which is coupled with a rotor 117. The rotor 117 may include an internal thread 118, configured to engage the thread of plunger 41 to facilitate coupling of the plunger 41 and rotor 117. The plunger 41 is fixed to the inner piece 39 of the actuator 9 such that the plunger does not rotate relative to the actuator 9. The rotor 117 interfaces with the thread, and therefore the plunger 41 causes the rotor 117 to rotate in the second rotational direction 75 as the plunger 41 moves distally with the actuator 9. The rotor 117 is coupled with damping element 45, which in this example is a torsion spring 119 that is biased towards a coiled state. As the rotor 117 rotates, the rotor 117 uncoils the torsion spring 119 which damps rotation of the rotor 117 and thus damps progression of the actuator 9 towards the distal position. The properties of the spring 119 may be selected according to the resistance desired. For example, if high resistance is desired, a spring 119 having a high spring constant may be selected.

The damping element 45 also comprises a ratchet 121 that comprises a plurality of angled teeth which interface with angled teeth 130 on the rotor 117. Once the actuator 9 is moved by a distance towards the distal position, the angled teeth of the rotor 117 are moved into engagement with the angled teeth of the ratchet 121. The rotor 117 and ratchet 121 form an anti-rotation mechanism that permits the rotor 117 to rotate in the second rotational direction 75, but resists movement of the rotor in the first rotational direction 57. In this way, the tension in the torsion spring 119 is maintained as the rotor 117 uncoils the spring 119, since the torsion spring 119 is prevented from moving back to its coiled state.

The angled teeth 130 of the rotor 117 may each include an angled edge 132 (e.g. angled with respect to the longitudinal axis of the trainer) and a straight edge 131 (e.g. substantially parallel with respect to the longitudinal axis of the trainer). The rotor 117 may be configured such that the angled edge of each tooth faces in the second rotational direction 75. In other words, the angled edge of each angled tooth leads when the rotor 117 is caused to rotate as the plunger 41 moves distally with the actuator 9. The angled teeth of the ratchet 121 approximately tessellate with the angled teeth of the rotor 117. In other words, the straight edges of each tooth of the ratchet 121 face in the second rotational direction 75, such that the straight edges of the teeth of the rotor 117 abut a respective straight edge of the teeth of the ratchet 121 to resist movement of the rotor in the first rotational direction 57. The ratchet 121 may be rotationally fixed relative to the actuator 9.

The damping element 45 and rotor 117 may be configured according to the point at which, during depression of the actuator, engagement of the rotor 117 and ratchet 121, and therefore formation of the anti-rotation mechanism, is desired. For example, in embodiments in which a spring 119 of high spring constant is used, it may be desirable for the anti-rotation mechanism to engage earlier in depression of actuator 9, to assist a user in resisting the biasing of spring 119 back to its coiled state. Earlier engagement of the anti-rotation mechanism earlier may be achieved, for example, by providing angled teeth of the ratchet 121 having a greater height along the longitudinal axis of the trainer 1.

When the actuator 9 is pulled rather than being pushed, or in other words when the actuator 9 is moved proximally, the plunger 41 moves the angled teeth of the rotor 117 out of engagement with the angled teeth of the ratchet 121. This permits the rotor to move in the first rotational direction 57 when the plunger 41 moves proximally which moves the spring back to the coiled state. The decoupling distance—the distance by which the actuator 9, plunger 41, and rotor 117 are moved proximally in order to move the angled teeth of the rotor 117 out of engagement with the angled teeth of the ratchet 121—is a distance greater than the height, along the longitudinal axis of the trainer 1, of the angled teeth of the ratchet. In some embodiments, the decoupling distance may be approximately 2 mm.

The damping element may be implemented in the trainer 1 in order to simulate a large volume and/or high viscosity dose. The damping element may also be utilised in injection devices, to force a user to depress the actuator 9 slowly when delivering a large dose or a substance of low viscosity (which, itself, may offer little resistance to depression) to mitigate harmful side effects of injecting a substance too quickly, such as excessive bruising, pain, pooling of the injected substance within the patient, etc.

In an alternative embodiment of the damping element, the torsion spring may be coupled to the ratchet. As in the previous embodiment, the rotor interfaces with the thread of the plunger, and therefore the plunger causes the rotor to rotate in the second rotational direction as the plunger moves distally with the actuator. In this embodiment, the rotor is configured such that the straight edges of each tooth face in the second rotational direction. In other words, the straight edge of each angled tooth leads when the rotor is caused to rotate as the plunger moves distally with the actuator. The initial rotation of the rotor in this embodiment does not cause uncoiling of the torsion spring. Hence, initial progression of the actuator towards the distal position is met by little, or no, resistance.

The alternative damping element comprises a ratchet coupled with the torsion spring that is biased towards a coiled state. The ratchet comprises a plurality of angled teeth which interface with angled teeth on the rotor. Once the actuator is moved by a distance towards the distal position, the angled teeth of the rotor are moved into engagement with the angled teeth of the ratchet, such that the straight edges of the teeth of the rotor rotate into abutment with a respective straight edge of the teeth of the ratchet. In this embodiment, once the rotor and ratchet have moved into engagement with one another, continued rotation of the rotor causes the ratchet to rotate. Rotation of the ratchet uncoils the torsion spring, which damps rotation of the ratchet and rotor and thus damps further progression of the actuator towards the distal position. Again, the configuration of the damping element and rotor, for example the spring properties and teeth height, may be selected according to the desired resistance profile.

In some embodiments, the rotor 117 and/or damping element 45 may be replaceable parts of a trainer or injection device. For example, the device may be configured such that torsion spring 119 may be replaced with another spring, of higher or lower spring constant. This facilitates, for example, a single trainer device to be used to train a user in delivering substances of various different viscosities.

An injection device in the context of this application may be an automatic injection device (an auto-injector). In such injection devices, the actuator 9 is operated by, or replaced by, an automated actuator such as a drive spring, a pneumatic piston operated by a compressed gas canister, or a solenoid, in an electrically powered automatic injection device.

In such auto-injector devices, the damping element 45 may be utilised to damp, slow or control the force applied by the actuator to a container which contains the substance to be injected and/or a delivery mechanism, e.g. a plunger on the drug container, such as a syringe. The damping element may be useful in tuning the speed of an injection by an auto-injector, without requiring alteration of the automated actuator.

The damping element may be configured to operate during any portion of the actuation sequence. For example, the damping element may be configured such that progression of an actuator towards the distal position is damped for the entire duration of the progression, or for only a select portion. In some embodiments, the injection device may be configured such that damping of progression of the actuator begins at the point of full extension of a needle on the drug container, for example to ensure full delivery of the injection substance by an auto-injector.

Unless otherwise indicated each embodiment as described herein may be combined with another embodiment as described herein.

It will be understood that the benefits and advantages described above may relate to one embodiment or may relate to several embodiments. The embodiments are not limited to those that solve any or all of the stated problems or those that have any or all of the stated benefits and advantages.

Any reference to "an" item refers to one or more of those items.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

Aspects of the Invention, Forming Part of the Description:

1. An injection device trainer for training a user to use an injection device, the injection device trainer comprising:
    a body portion;
    an actuator positioned towards a proximal end of the body portion, the actuator moveable from a proximal position to a distal position;
    a shield positioned towards a distal end of the body portion, the shield moveable between: an initial position; a retracted position that is more proximal relative to the body portion than the initial position; and an extended position that is more distal relative to the body portion than the initial position; and
    a locking member adapted to be rotatable between a first orientation in which the locking member resists movement of the actuator from the proximal position to the distal position; and a second orientation in which the locking member permits the actuator to move from the proximal position to the distal position;
    wherein the first orientation of the locking member is configured to hold the shield in the initial position such that the shield is prevented from moving from the initial position to the extended position, and permits movement of the shield from the initial position to the retracted position;
    wherein the shield is configured to contact with the locking member when moving from the initial position to the retracted position in order to move the locking member from the first orientation to the second orientation; and
    wherein movement of the actuator by a first distance towards the distal position is configured to unlock the shield from the locking member such that the shield is allowed to move towards the extended position.

2. The injection device trainer of aspect 1, wherein the locking member comprises at least one actuator resistance surface, and the actuator comprises at least one abutment surface; and
    wherein the at least one actuator resistance surface is arranged to abut with the at least one abutment surface so as to resist movement of the actuator from the proximal position to the distal position when the locking member is in the first orientation.

3. The injection device trainer of aspect 1 or aspect 2, wherein the locking member comprises a pair of actuator resistance surfaces, and the actuator comprises a pair of abutment surfaces; and
    wherein each one of the pair of actuator resistance surfaces are arranged to abut a respective one of the pair of abutment surfaces so as to resist movement of the actuator from the proximal position to the distal position when the locking member is in the first orientation.

4. The injection device trainer of aspect 3, wherein the pair of actuator resistance surfaces are located on opposite sides of the locking member with respect to one another.

5. The injection device trainer of aspect 3 or aspect 4, wherein the locking member comprises a cylindrical housing, and each one of the pair of actuator resistance surfaces comprises a protrusion that protrudes from the surface of the cylindrical housing.

6. The injection device trainer of aspect 5, wherein the pair of abutment surfaces are located on opposite sides of the actuator with respect to one another.

7. The injection device trainer of any one of the preceding aspects, wherein the locking member comprises a ramp; and the shield comprises a ramp interface configured to interact with the ramp when the locking member moves from the initial position to the retracted position, thus rotating the locking member from the first orientation to the second orientation.

8. The injection device trainer of any one of the preceding aspects, wherein the locking member comprises a third orientation in which the shield is allowed to move from the initial position to the extended position.

9. The injection device trainer of aspect 8, wherein the actuator is configured to move by a first distance in order to move the locking member into the third orientation.

10. The injection device trainer of aspect 8 or aspect 9, wherein the locking member comprises a deflector portion; and the actuator is arranged to interface with the deflector portion to move the locking member from the second orientation to the third orientation.

11. The injection device trainer of any one of the preceding aspects, wherein the locking member comprises a stop that is arranged to sit within a recess in the shield, thus holding the shield in the initial position.

12. The injection device trainer of aspect 11, wherein the stop is arranged to move along a slot in the shield in order to allow the shield to move to the extended position.

13. The injection device trainer of aspect 12, wherein the stop is arranged to sit outside of the slot in the recess thus holding the shield in the initial position when the locking member is in the first orientation.

14. The injection device trainer of aspect 12 or aspect 13, wherein the locking member comprises a third orientation in which the shield is allowed to move from the initial position to the extended position; and movement of the locking member from the second orientation to the third orientation pushes the stop into the slot which permits the shield to move from the initial position to the extended position.

15. The injection device trainer of any one of aspects 11 to 14, wherein the stop is coupled to a resilient member that is configured to bend in order to move the stop inwards from a resting state towards the longitudinal axis of the trainer into a flexed state.

16. The injection device trainer of aspect 15, wherein the stop in the resting state holds the shield in the initial position.

17. The injection device trainer of aspect 15 or aspect 16, wherein the stop in the flexed state permits the stop to move into the slot.

18. The injection device trainer of any one of the preceding aspects, further comprising a biasing element arranged to bias the shield to move distally.

19. The injection device trainer of any one of the preceding aspects, wherein the locking member has a fourth orientation in which the locking member resists the shield from moving from the extended position to the initial position.

20. The injection device trainer of aspect 19, further comprising a biasing element arranged to bias the locking member towards the fourth orientation such that once the actuator has moved a distance towards the distal position and the shield is in the extended position the locking member moves into the fourth orientation.

21. The injection device trainer of aspect 20, wherein the biasing element comprises a torsion spring.

22. The injection device trainer of any one of aspects 19 to 21, wherein the actuator is configured to interface with the locking member when moving from the distal position to the proximal position to move the locking member from the fourth orientation towards the first orientation thus allowing the shield to move from the extended position to the initial position.

23. The injection device trainer of any one of aspects 19 to 22, wherein the locking member comprises a shield resistance surface that is arranged to resist proximal movement of the shield when the locking member is in the fourth orientation and the shield is in the extended position.

24. The injection device trainer of aspect 23, wherein the shield comprises an abutment surface arranged to abut the shield resistance surface when the locking member is in the fourth orientation and the shield is in the extended position.

25. The injection device of any one of the preceding aspects, wherein the proximal position of the actuator simulates an unactivated position of a plunger of an injection device.

26. The injection device of any one of the preceding aspects, wherein the distal position of the actuator simulates an activated position of a plunger of an injection device.

27. The injection device of any one of the preceding aspects, wherein the initial position of the shield simulates covering of a needle of an injection device.

28. The injection device of any one of the preceding aspects, wherein the retracted position of the shield simulates exposing a needle of an injection device.

29. The injection device of any one of the preceding aspects, wherein the extended position of the shield simulates a locked-out state of an injection device in which the shield is prevented from exposing a needle.

30. The injection device trainer of any one of the preceding aspects, wherein:
the actuator is coupled with a rotor, such that movement of actuator from the proximal position to the distal position causes the rotor to rotate; and
the injection device trainer further comprises a damping element coupled or coupleable to the rotor in order to damp the rotation of the rotor.

31. An injection device comprising:
a needle coupled with a chamber for storing fluid;
a body portion;
an actuator positioned towards a proximal end of the body portion, the actuator moveable from a proximal position to a distal position for dispensing fluid stored in the chamber from the needle;
a shield positioned towards a distal end of the body portion, the shield moveable between: an initial position in which the shield covers the needle; a retracted position in which the shield exposes the needle, wherein the retracted position is more proximal relative to the body portion than the initial position; and an extended position in which the shield covers the needle, wherein the extended position is more distal relative to the body portion than the initial position; and
a locking member rotatable between a first orientation in which the locking member resists movement of the actuator from the proximal position to the distal position; and a second orientation in which the locking member permits the actuator to move from the proximal position to the distal position;
wherein the first orientation of the locking member is configured to hold the shield in the initial position such that the shield is prevented from moving from the initial position to the extended position, and permits movement of the shield from the initial position to the retracted position;
the shield is configured to contact the locking member when moving from the initial position to the retracted position in order to move the locking member from the first orientation to the second orientation; and
movement of the actuator by a first distance towards the distal position unlocks the shield from the locking member such that the shield is allowed to move towards the extended position.

32. The injection device of claim 31, wherein:
the actuator is coupled with a rotor, such that movement of actuator from the proximal position to the distal position causes the rotor to rotate; and
the injection device further comprises a damping element coupled or coupleable to the rotor in order to damp the rotation of the rotor.

33. A kit of parts configured for assembly into an injection device trainer of any one of aspects 1 to 30 or an injection device of aspect 31 or 32.

34. A method for training a user to use an injection device, the method comprising providing an injection device trainer comprising:
a body portion;
an actuator positioned towards a proximal end of the body portion, the actuator moveable from a proximal position to a distal position;
a shield positioned towards a distal end of the body portion, the shield moveable between: an initial position; a retracted position that is more proximal relative to the body portion than the initial position; and an extended position that is more distal relative to the body portion than the initial position; and a locking member rotatable between a first orientation in which the locking member resists movement of the actuator from the proximal position to the distal position; and a second orientation in which the locking member permits the actuator to move from the proximal position to the distal position;

wherein the first orientation of the locking member is configured to hold the shield in the initial position such that the shield is prevented from moving from the initial position to the extended position, and permits movement of the shield from the initial position to the retracted position; and the method further comprises:

moving the shield from the initial position to the retracted position so that the shield contacts with the locking member in order to move the locking member from the first orientation to the second orientation; and moving the actuator by a first distance towards the distal position to unlock the shield from the locking member such that the shield moves towards the extended position.

35. The method of aspect 34, wherein:

the actuator is coupled with a rotor, such that movement of actuator from the proximal position to the distal position causes the rotor to rotate;

the injection device trainer further comprises a damping element coupleable to the rotor in order to damp the rotation of the rotor; and the method further comprises moving the actuator from the proximal position to the distal position during which the damping element damps rotation of the rotor and thus damps movement of the actuator towards the distal position.

36. A method of administering an injection, the method comprising providing an injection device comprising:

a needle coupled with a chamber for storing fluid;

a body portion;

an actuator positioned towards a proximal end of the body portion, the actuator moveable from a proximal position to a distal position for dispensing fluid stored in the chamber from the needle;

a shield positioned towards a distal end of the body portion, the shield moveable between: an initial position in which the shield covers the needle; a retracted position in which the shield exposes the needle, wherein the retracted position is more proximal relative to the body portion than the initial position; and an extended position in which the shield covers the needle, wherein the extended position is more distal relative to the body portion than the initial position; and a locking member rotatable between a first orientation in which the locking member resists movement of the actuator from the proximal position to the distal position; and a second orientation in which the locking member permits the actuator to move from the proximal position to the distal position;

wherein the first orientation of the locking member is configured to hold the shield in the initial position such that the shield is prevented from moving from the initial position to the extended position, and permits movement of the shield from the initial position to the retracted position; and the method further comprises:

moving the shield from the initial position to the retracted position so that the shield contacts the locking member in order to move the locking member from the first orientation to the second orientation; and moving the actuator by a first distance towards the distal position to unlock the shield from the locking member such that the shield moves towards the extended position.

37. The method of aspect 36, wherein:

the actuator is coupled with a rotor, such that movement of actuator from the proximal position to the distal position causes the rotor to rotate;

the injection device further comprises a damping element coupleable to the rotor in order to damp the rotation of the rotor; and the method further comprises moving the actuator from the proximal position to the distal position during which the damping element damps rotation of the rotor and thus damps movement of the actuator towards the distal position.

The invention claimed is:

1. An injection device trainer for training a user to use an injection device, the injection device trainer comprising:

a body portion;

an actuator positioned towards a proximal end of the body portion, the actuator moveable from a proximal position to a distal position;

a shield positioned towards a distal end of the body portion, the shield moveable between: an initial position; a retracted position that is more proximal relative to the body portion than the initial position; and an extended position that is more distal relative to the body portion than the initial position; and a locking member adapted to be rotatable between a first orientation in which the locking member resists movement of the actuator from the proximal position to the distal position; and a second orientation in which the locking member permits the actuator to move from the proximal position to the distal position;

wherein the first orientation of the locking member is configured to hold the shield in the initial position such that the shield is prevented from moving from the initial position to the extended position, and permits movement of the shield from the initial position to the retracted position;

wherein the shield is configured to contact with the locking member when moving from the initial position to the retracted position in order to move the locking member from the first orientation to the second orientation; and wherein movement of the actuator by a first distance towards the distal position is configured to unlock the shield from the locking member such that the shield is allowed to move towards the extended position.

2. The injection device trainer of claim 1 wherein the locking member comprises at least one actuator resistance surface, and the actuator comprises at least one abutment surface; and wherein the at least one actuator resistance surface is arranged to abut with the at least one abutment surface so as to resist movement of the actuator from the proximal position to the distal position when the locking member is in the first orientation.

3. The injection device trainer of claim 1 wherein the locking member comprises a pair of actuator resistance surfaces, and the actuator comprises a pair of abutment surfaces; and wherein each one of the pair of actuator resistance surfaces are arranged to abut a respective one of the pair of abutment surfaces so as to resist movement of the actuator from the proximal position to the distal position when the locking member is in the first orientation.

4. The injection device trainer of claim 3, wherein the pair of actuator resistance surfaces are located on opposite sides of the locking member with respect to one another.

5. The injection device trainer of claim 3, wherein the locking member comprises a cylindrical housing, and each one of the pair of actuator resistance surfaces comprises a protrusion that protrudes from a surface of the cylindrical housing.

6. The injection device trainer of claim 5, wherein the pair of abutment surfaces are located on opposite sides of the actuator with respect to one another.

7. The injection device trainer of claim 1, wherein the locking member comprises a ramp; and the shield comprises a ramp interface configured to interact with the ramp when the shield moves from the initial position to the retracted position, thus rotating the locking member from the first orientation to the second orientation.

8. The injection device trainer of claim 1, wherein the locking member comprises a third orientation in which the shield is allowed to move from the initial position to the extended position.

9. The injection device trainer of claim 8, wherein the actuator is configured to move by the first distance in order to move the locking member into the third orientation.

10. The injection device trainer of claim 8, wherein the locking member comprises a deflector portion; and the actuator is arranged to interface with the deflector portion to move the locking member from the second orientation to the third orientation.

11. The injection device trainer of claim 1, wherein the locking member comprises a stop that is arranged to sit within a recess in the shield, thus holding the shield in the initial position.

12. The injection device trainer of claim 11, wherein the stop is arranged to move along a slot in the shield in order to allow the shield to move to the extended position.

13. The injection device trainer of claim 12, wherein the stop is arranged to sit outside of the slot in the recess thus holding the shield in the initial position when the locking member is in the first orientation.

14. The injection device trainer of claim 12, wherein the locking member comprises a third orientation in which the shield is allowed to move from the initial position to the extended position; and movement of the locking member from the second orientation to the third orientation pushes the stop into the slot which permits the shield to move from the initial position to the extended position.

15. The injection device trainer of claim 11, wherein the stop is coupled to a resilient member that is configured to bend in order to move the stop inwards from a resting state towards a longitudinal axis of the trainer into a flexed state.

16. The injection device trainer of claim 15, wherein the stop in the resting state holds the shield in the initial position.

17. The injection device trainer of claim 15, wherein the stop in the flexed state permits the stop to move into the slot.

18. The injection device trainer of claim 1, further comprising a biasing element arranged to bias the shield to move distally.

19. The injection device trainer claim 1, wherein the locking member has a fourth orientation in which the locking member resists the shield from moving from the extended position to the initial position.

20. The injection device trainer of claim 19, further comprising a biasing element arranged to bias the locking member towards the fourth orientation such that once the actuator has moved a distance towards the distal position and the shield is in the extended position the locking member moves into the fourth orientation.

21. The injection device trainer of claim 20, wherein the biasing element comprises a torsion spring.

22. The injection device trainer of claim 19, wherein the actuator is configured to interface with the locking member when moving from the distal position to the proximal position to move the locking member from the fourth orientation towards the first orientation thus allowing the shield to move from the extended position to the initial position.

23. The injection device trainer of claim 19, wherein the locking member comprises a shield resistance surface that is arranged to resist proximal movement of the shield when the locking member is in the fourth orientation and the shield is in the extended position.

24. The injection device trainer of claim 23, wherein the shield comprises an abutment surface arranged to abut the shield resistance surface when the locking member is in the fourth orientation and the shield is in the extended position.

25. The injection device trainer of claim 1, wherein the proximal position of the actuator simulates an unactivated position of a plunger of an injection device.

26. The injection device trainer of claim 1, wherein the distal position of the actuator simulates an activated position of a plunger of an injection device.

27. The injection device trainer of claim 1, wherein the initial position of the shield simulates covering of a needle of an injection device.

28. The injection device trainer of claim 1, wherein the retracted position of the shield simulates exposing a needle of an injection device.

29. The injection device trainer of claim 1, wherein the extended position of the shield simulates a locked-out state of an injection device in which the shield is prevented from exposing a needle.

30. The injection device trainer of claim 1, wherein:
the actuator is coupled with a rotor, such that movement of the actuator from the proximal position to the distal position causes the rotor to rotate; and
the injection device trainer further comprises a damping element coupled to or coupleable to the rotor in order to damp the rotation of the rotor.

31. A kit of parts configured to be assembled to form the injection device trainer of claim 1.

32. A method of using an injection device trainer, the injection device trainer comprising:
a body portion;
an actuator positioned towards a proximal end of the body portion, the actuator moveable from a proximal position to a distal position;
a shield positioned towards a distal end of the body portion, the shield moveable between: an initial position; a retracted position that is more proximal relative to the body portion than the initial position; and an extended position that is more distal relative to the body portion than the initial position; and
a locking member rotatable between a first orientation in which the locking member resists movement of the actuator from the proximal position to the distal position; and a second orientation in which the locking member permits the actuator to move from the proximal position to the distal position;
wherein the first orientation of the locking member is configured to hold the shield in the initial position such that the shield is prevented from moving from the initial position to the extended position, and permits movement of the shield from the initial position to the retracted position; and wherein the method comprises:

moving the shield from the initial position to the retracted position so that the shield contacts with the locking member in order to move the locking member from the first orientation to the second orientation; and moving the actuator by a first distance towards the distal position to unlock the shield from the locking member such that the shield moves towards the extended position.

33. The method of claim 32, wherein:

the actuator is coupled with a rotor, such that movement of the actuator from the proximal position to the distal position causes the rotor to rotate;

the injection device trainer further comprises a damping element coupleable to the rotor in order to damp the rotation of the rotor; and the method further comprises moving the actuator from the proximal position to the distal position during which the damping element damps rotation of the rotor and thus damps movement of the actuator towards the distal position.

34. An injection device trainer for training a user to use an injection device, the injection device trainer comprising:

a body portion;

an actuator positioned towards a proximal end of the body portion, the actuator configured to be gripped by a user to move the actuator from a proximal position to a distal position, wherein the actuator is coupled with a rotor, such that movement of the actuator from the proximal position to the distal position causes the rotor to rotate; and a damping element coupled to or coupleable to the rotor in order to damp the rotation of the rotor and thereby damp movement of the actuator towards the distal position; and a shield positioned towards a distal end of the body portion, the shield moveable relative to the body portion between an initial position, and a retracted position that is more proximal relative to the body portion than the initial position.

35. The injection device trainer of claim 34, wherein:

the actuator has a plunger with a thread; and the rotor includes an internal thread configured to engage the thread of the plunger.

36. The injection device trainer of claim 34, wherein the damping element is a torsion spring that is biased towards a coiled state, and as the rotor rotates, the rotor uncoils the torsion spring which damps rotation of the rotor and thus damps progression of the actuator towards the distal position.

37. The injection device trainer of claim 34, wherein the damping element comprises a ratchet that comprises a plurality of angled teeth that interface with angled teeth on the rotor to form an anti-rotation mechanism that permits the rotor to rotate in a select rotational direction but resists rotation of the rotor in a rotational direction opposite the select rotational direction.

38. A method of using an injection device trainer, the method comprising:

a user gripping an actuator of the injection device trainer, the actuator positioned towards a proximal end of a body portion of the injection device trainer; and a user pushing on the actuator to move the actuator relative to the body portion from a proximal position to a distal position such that movement of the actuator from the proximal position to the distal position causes 1) a rotor of the injection device trainer to rotate and 2) a damping element of the injection device trainer to damp rotation of the rotor, thereby damping movement of the actuator towards the distal position, wherein the method comprises, prior to moving the actuator, moving a shield of the injection device trainer that is positioned towards a distal end of the body portion such that the shield moves between an initial position, and a retracted position that is more proximal relative to the body portion than the initial position.

39. The method of claim 38, wherein movement of the actuator from the proximal position to the distal position causes threads of a plunger of the actuator to engage internal threads of the rotor to cause the rotor to rotate.

40. The method of claim 38, wherein the damping element is a torsion spring that is biased towards a coiled state, and movement of the actuator from the proximal position to the distal position causes the rotor to uncoil the torsion spring to damp rotation of the rotor.

* * * * *